United States Patent [19]

Sasagawa

[11] Patent Number: 5,086,057
[45] Date of Patent: Feb. 4, 1992

[54] METHOD OF TREATING CACHEXIA AND CERTAIN NEW COMPOUNDS FOR USE IN THIS METHOD

[75] Inventor: Yo Takiguchi, Jun Ohsumi, Yasuo Shimoji, Kazuhiko Sasagawa, all of Tokyo, Japan

[73] Assignee: Sankyo Company Limited, Tokyo, Japan

[21] Appl. No.: 691,542

[22] Filed: Apr. 25, 1991

Related U.S. Application Data

[62] Division of Ser. No. 365,851, Jun. 14, 1989.

[30] Foreign Application Priority Data

Jun. 16, 1988 [JP] Japan .................................. 63-149137

[51] Int. Cl.$^5$ .................... A01N 43/54; A01N 43/647; A61K 31/505; C07D 239/70
[52] U.S. Cl. ...................................... 514/267; 514/411; 544/252
[58] Field of Search ................. 514/359, 411; 544/245, 544/249, 251, 252, 267

[56] References Cited

U.S. PATENT DOCUMENTS 4,007,189  2/1977  Sato et al. ............................ 544/251
4,619,933 10/1986  Stringfellow et al. ................ 514/272

FOREIGN PATENT DOCUMENTS 52-116496  9/1977  Japan .
53-53697   5/1978  Japan .

OTHER PUBLICATIONS

Sato et al.—"Studies on Cardiovascular Agents, 6, Synthesis and Coronary Vasodilating and Antihypetensive Activities of 1, 2, 4-Triazolo[1,5-a]pyrimidines Fused to Heterocyclic Systems",—J. Med. Chem. 23, 1927-1938 (1980) pp. 927-937.

*Primary Examiner*—Thurman K. Page
*Assistant Examiner*—C. Azpuru
*Attorney, Agent, or Firm*—Frishauf, Holtz, Goodman & Woodward

[57] ABSTRACT

Compounds of formula (I):

(I)

[in which:
Y represents a group of formula (II)

or (III)

the dotted line is a double of single bond; $R^1$ is hydrogen, alkyl or aryl; $R^2$ is hydrogen or halogen; $R^3$ is alkyl or cycloalkyl; $R^4$ is hydrogen, alkyl, hydroxy or halogen; and $R^6$ is hydrogen, optionally substituted alkyl, alkenyl, alkynyl, cycloalkyl, aryl, or aralkyl;]
and pharmaceutically acceptable salts thereof are valuable in the treatment of cachexia. Certain of these compounds are novel.

8 Claims, No Drawings

METHOD OF TREATING CACHEXIA AND CERTAIN NEW COMPOUNDS FOR USE IN THIS METHOD

This is a division of application Ser. No. 07/365,851 filed June 14, 1989, now abandoned.

BACKGROUND TO THE INVENTION

The present invention relates to the use of a series of triazolopyrimidine and pyrazolopyrimidine derivatives as therapeutic agents for the treatment of cachexia, and also provides certain such compounds as novel compositions of matter and provides processes for the preparation of the aforesaid new compounds.

Certain of the triazolopyrimidine compounds used in the present invention are disclosed in Japanese Patent Application Kokai (i.e. as laid open to public inspection prior to examination) No. Sho 51-141896 [Tokko (i.e. as published after examination) No. Sho 57-60356], Japanese Patent Application Kokai No. Sho 52-116497 (Tokko No. Sho 58-437), Japanese Patent Application Kokai No. Sho 53-53697, U.S. Pat. No. 4,007,189 and the Journal of Medicinal Chemistry, 23, 927–937 (1980). In addition certain ketonic compounds of this type were disclosed orally at a meeting of the Pharmaceutical Society of Japan on 28–30 Aug. 1979 and were reported to be of use in the treatment of ischemic heart disease. However, it has not previously been found that any of these known compounds have properties which might render them suitable for the treatment of cachexia.

"Cachexia" is the name given to a generally weakened condition of the body or mind resulting from any debilitating chronic disease. The symptoms include severe weight loss, anorexia and anemia. Cachexia is normally associated with neoplasmic diseases, chronic infectious diseases or thyroiditis, and is a particular problem when associated with cancerous conditions.

Indeed, it has been reported that a large proportion of the deaths resulting from cancer are, in fact, associated with cachexia, as also are various other problems commonly experienced by cancer patients, such as respiratory insufficiency, cardiac failure, diseases of the digestive organs, hemorrhaging and systemic infection [U. Cocchi, Strahlentherapie, 69, 503–520 (1941); K. Utsumi et al., Jap. J. Cancer Clinics, 7, 271–283 (1961)].

Cancer associated cachexia, which decreases the tolerance of cancer patients to chemotherapy and radiotherapy, is said to be one of the obstacles to effective cancer therapy [J. T. Dwyer, Cancer, 43, 2077–2086 (1979); S. S. Donaldson et al., Cancer, 43, 2036–2052 (1979)]. In order to overcome these problems, it used to be common for cancer patients with cachexia to receive a high fat and high sugar diet, or they used to be given high calorie nutrition intravenously. However, it has been reported that symptoms of cachexia were rarely alleviated by these regimens [M. F. Brenann, Cancer Res., 37, 2359–2364 (1977): V. R. Young, Cancer Res., 37, 2336–2347 (1977)].

There are several papers referring to the causes of cachexia. Thus, it has been reported that, in cachexia associated with infection by bacteria or protozoa, certain humoral factors, such as cachectin/TNF (Tumor Necrosis Factor), interleukin I or γ-interferon, may suppress the activity of enzymes such as lipoprotein lipase (E.C.3.1.1.34), which is an essential enzyme for triglyceride metabolism, and acetyl CoA carboxylase and fatty acid synthetase, which are rate determining enzymes in fatty acid synthesis. The same paper also points out that any disorder involving the metabolism of fat may lead the patients to experience severe waste and weight loss [M. Kawakami et al., J. Exp. Med., 154, 631–639 (1981); B. Beutler et al., Nature, 320, 584–588 (1986); B. Beutler et al., J. Immunol., 135, 3969–3971 (1985); R. Kurzrock et al., J. Exp. Med., 164, 1093–1101 (1986); P. H. Pekala et al., Proc. Natl. Acad. Sci. U.S.A., 80, 2743–2747 (1983); S. R. Price et al., Arch. Biochem. Biophys., 251, 738–746 (1986); M. Kawakami, Med. Immunol. 14, 187–190 (1987); J. S. Patton et al., Proc. Natl. Acad. Sci. U.S.A., 83, 8313–8317 (1986)].

On the other hand, it is well known that cancer associated cachexia often results in the depletion of stored body-fat. This depletion is one of the major causes of systemic waste in cancer patients. It has also been suggested that this depletion of body-fat is brought about by increasing the removal of fatty acids from the adipose tissue of cancer patients [A. Theologides, Cancer, 43, 2004–2012 (1979)]. Another paper has reported a correlation between cachexia and a reduction in the activity of plasma lipoprotein lipase [H. Vlassara et al., Horm. Metabol. Res., 18, 698–703 (1986)].

However, on the contrary, there has also been reported an increase in the activity of the plasma lipoprotein lipase in cancer patients suffering from cachexia [H. Masuno et al., Jap. J. Cancer Res., 76, 202–207 (1985)].

Accordingly, the relationship between cachexia and lipoprotein lipase has so far not been definitely established, and there are, indeed, contradictory indications as to whether or not it might be implicated.

We have now discovered that lipoprotein lipase is a key enzyme in cachexia therapy, and that the cachexia in mammals, and hence in humans, may be alleviated by the enhancement of the activity of this enzyme. This enzyme is able to hydrolyze triglyceride in the very low density lipoprotein and the chylomicron to convert the circulating triglyceride to the stored form. We have accordingly provided certain compounds, some of which are new and some of which are known, but all of which have not previously been known to enhance the activity of lipoprotein lipase, and which, by such enhancement, have demonstrated the ability to alleviate the effects of cachexia.

BRIEF SUMMARY OF INVENTION

Thus, the present invention provides a method of treating or alleviating the effects of cachexia by the administration to a mammal, which may be human, suffering from cachexia of an effective amount of an active agent, wherein the active agent is at least one enhancer of the activity of lipoprotein lipase selected from the group consisting of compounds of formula (I):

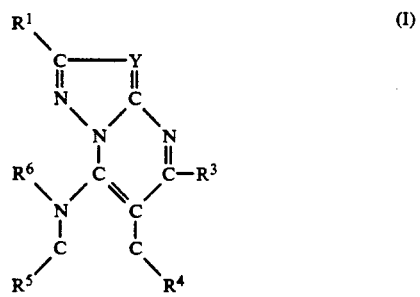

in which:

Y represents a group of formula $$\begin{array}{c}\diagdown\\ \phantom{a}\diagup\end{array}\!\!\!\!\!\!\!\!N \qquad \text{(II)}$$

or $$\begin{array}{c}\diagdown\\ \phantom{a}\diagup\end{array}\!\!\!\!\!\!\!\!C\!-\!R^2; \qquad \text{(III)}$$

the dotted line represents a carbon-carbon double bond or a carbon-carbon single bond and, if necessary, a hydrogen atom at one or both of the carbon atoms which the bond links;

$R^1$ represents a hydrogen atom, a $C_1$–$C_5$ alkyl group or a $C_6$–$C_{10}$ carbocyclic aryl group which is unsubstituted or has at least one substituent selected from the group consisting of substituents (a), defined below;

$R^2$ represents a hydrogen atom or a halogen atom;

$R^3$ represents a $C_1$–$C_5$ alkyl group or a $C_3$–$C_7$ cycloalkyl group;

$R^4$ represents a hydrogen atom, a $C_1$–$C_5$ alkyl group or a hydroxy group, or, but only when Y represents said group of formula (III) and said dotted line represents a double bond, a halogen atom;

$R^5$ represents a hydrogen atom, a $C_1$–$C_5$ alkyl group, a hydroxy group, an oxygen atom or, but only when Y represents said group of formula (III) and said dotted line represents a double bond, a halogen atom; and $R^6$ represents a hydrogen atom, a $C_1$–$C_{15}$ alkyl group, a $C_1$–$C_5$ alkyl group having at least one substituent selected from the group consisting of substituents (b), defined below, a $C_3$–$C_7$ alkenyl group, a $C_3$–$C_5$ alkynyl group, a $C_3$–$C_{10}$ cycloalkyl group, a $C_6$–$C_{10}$ carbocyclic aryl group which is unsubstituted or has at least one substituent selected from the group consisting of substituents (a), defined below, or an aralkyl group in which the alkyl part is $C_1$–$C_3$ and is unsubstituted or has at least one hydroxy substituent, and the aryl part is a $C_6$–$C_{10}$ carbocyclic aryl group which is unsubstituted or has at least one substituent selected from the group consisting of substituents (c), defined below;

Substituents (a)

$C_1$–$C_5$ alkyl groups, halogen atoms, $C_1$–$C_5$ alkoxy groups and sulfamoyl groups;

Substituents (b)

Halogen atoms, hydroxy groups, mercapto groups, dialkylamino groups in which each alkyl part is $C_1$–$C_5$ and is unsubstituted or has at least one hydroxy substituent, heterocyclic groups as defined below, phenoxy groups, $C_1$–$C_5$ alkoxy groups, $C_1$–$C_5$ hydroxyalkoxy groups, benzoyl groups, substituted benzoyl groups having at least one substituent selected from the group consisting of substituents (d), defined below, benzoyloxy groups, substituted benzoyloxy groups having at least one substituent selected from the group consisting of substituents (d), defined below, and heterocyclic-carbonyloxy groups in which the heterocyclic part has from 5 to 6 ring atoms of which 1 or 2 are nitrogen hetero-atoms;

Substituents (c)

$C_1$–$C_5$ alkyl groups, halogen atoms and $C_1$–$C_5$ alkoxy groups;

Substituents (d)

Halogen atoms and $C_1$–$C_5$ alkoxy groups;

said heterocyclic groups have from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said group being unsubstituted or having at least one $C_1$–$C_5$ alkyl substituent;

and pharmaceutically acceptable salts thereof.

Of the compounds listed above, those compounds are novel in which Y represents the group of formula (III), and these new compounds also form part of the present invention.

The invention also provides processes for preparing the novel compounds of the present invention, as described in more detail hereafter.

DETAILED DESCRIPTION OF INVENTION

A class of compounds which may be used in the present invention, and all of which are previously known as described above, is those compounds of formula (Ia):

$$\begin{array}{c} R^{5'} \diagdown \phantom{aaa} R^{6'} \\ HC\!-\!N \diagup \\ | \phantom{aaaa} | \\ HC \phantom{aaa} C \\ R^{4'}\!\diagup \diagdown \phantom{a} \diagup \diagdown \\ \phantom{aa} C \phantom{aa} N\!-\!N \\ | \phantom{aaaa} | \phantom{aaa} \| \\ \phantom{aa} C \phantom{aa} C \\ R^3 \diagup \diagdown N \diagup \diagdown N \diagup \diagdown R^1 \end{array} \qquad \text{(Ia)}$$

in which:

$R^1$ and $R^3$ are as defined above;

$R^{4'}$ represents a hydrogen atom, a hydroxy group or a $C_1$–$C_5$ alkyl group;

$R^{5'}$ represents a hydrogen atom, a hydroxy group, an oxygen atom or a $C_1$–$C_5$ alkyl group; and $R^{6'}$ represents a hydrogen atom, a $C_1$–$C_{15}$ alkyl group, a $C_1$–$C_5$ alkyl group having at least one substituent selected from the group consisting of substituents (b), defined above, a $C_3$–$C_7$ alkenyl group, a $C_3$–$C_{10}$ cycloalkyl group, a $C_6$–$C_{10}$ carbocyclic aryl group which is unsubstituted or has at least one substituent selected from the group consisting of substituents (a), defined above, or an aralkyl group in which the alkyl part is $C_1$–$C_3$ and the aryl part is a $C_6$–$C_{10}$ carbocyclic aryl group which is unsubstituted or has at least one substituent selected from the group consisting of substituents (c), defined above;

and pharmaceutically acceptable salts thereof.

In the above formula (Ia), and also in following formula (Ib), the groups shown as $R^{4'}$, $R^{4''}$, $R^{5'}$, $R^{5''}$ and $R^{6'}$ correspond to the groups shown in formula (I) as $R^4$, $R^5$ and $R^6$, respectively, and hereafter, where examples are given of groups which may be represented by $R^4$, $R^5$ and $R^6$, these examples apply mutatis mutandis to the groups represented by $R^{4'}$, $R^{4''}$, $R^{5'}$, $R^{5''}$ and $R^{6'}$.

Novel compounds of the present invention are those compounds of formula (Ib):

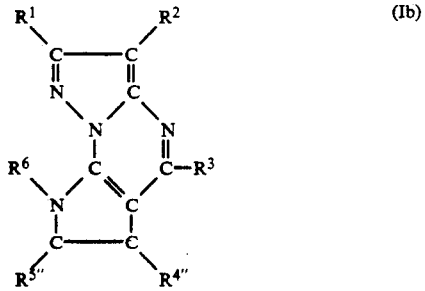

in which:

$R^1$, $R^2$, $R^3$, $R^6$ and the dotted line are as defined above.

$R^{4''}$ represents a hydrogen atom, or, but only when the dotted line represents a double bond, a hydrogen atom or a halogen atom; and $R^{5''}$ represents a hydrogen atom, or, but only when the dotted line represents a double bond, a hydrogen atom or a halogen atom;

and pharmaceutically acceptable salts thereof.

These novel compounds per se also form part of the present invention.

In the compounds of the invention, where $R^1$, $R^3$, $R^4$, $R^5$, substituent (a), substituent (c) and/or the alkyl substituent on the heterocyclic carbonyloxy group included within substituent (b) represents an alkyl group, this may be a straight or branched chain alkyl group containing from 1 to 5 carbon atoms. Examples of such groups include the methyl, ethyl, propyl, isopropyl, butyl, isobutyl, sec-butyl, t-butyl and pentyl groups. Of these, the straight and branched chain alkyl groups containing from 1 to 3 carbon atoms are preferred; and we most prefer that $R^1$ and/or $R^3$ and/or $R^4$ should represent a methyl group and that $R^5$ should represent a methyl or ethyl group.

Where $R^1$ and/or $R^6$ represents an aryl group, this is a carbocyclic aryl group containing from 6 to 10 ring carbon atoms, for example, a phenyl or naphthyl (1- or 2-naphthyl) group. This aryl group may be substituted or unsubstituted and, if it is substituted, the substituents are selected from the group consisting of substituents (a) defined above and exemplified below. There is, in general, no restriction on the number of substituents, except such as may be imposed by the number of substitutable positions, although sometimes steric constraints may further limit the number of such substituents; in general, the maximum number of substituents is 5 where the aryl group is a phenyl group and 7 where the aryl group is a naphthyl group. More preferably, $R^1$ and/or $R^6$ represents a phenyl group, which is unsubstituted or which has at least one substituent selected from the group consisting of: alkyl groups containing from 1 to 3 carbon atoms; halogen atoms; straight and branched chain alkoxy groups containing from 1 to 3 carbon atoms; and sulfamoyl groups. Most preferably, $R^1$ represents a phenyl group, which is unsubstituted or which has at least one substituent selected from the group consisting of halogen atoms and straight and branched chain alkoxy groups containing from 1 to 3 carbon atoms. $R^6$ most preferably represents a phenyl group, which is unsubstituted or which has at least one substituent selected from the group consisting of halogen atoms and sulfamoyl groups. Where $R^1$ and/or $R^6$ represents a substituted aryl group, examples of such groups include: aryl groups substituted with a straight or branched chain alkyl group containing from 1 to 5 carbon atoms, such as the 4-methylphenyl, 4-ethylphenyl and 3-propylphenyl groups; halogen-substituted aryl groups, such as the 4-chlorophenyl, 2,6-dichlorophenyl, 4-bromophenyl and 4-fluorophenyl groups; aryl groups substituted with a straight or branched chain alkoxy group containing from 1 to 5 carbon atoms, such as the 4-methoxyphenyl, 3,4-dimethoxyphenyl, 3,4,5-trimethoxyphenyl, 4-ethoxyphenyl and 4-propoxyphenyl groups; and sulfamoyl-substituted aryl groups, such as the 4-sulfamoylphenyl and 3-sulfamoylphenyl groups.

Examples of the groups and atoms which may be included in substituents (a) include:

(1) straight and branched chain alkyl groups containing from 1 to 5 carbon atoms, such as the methyl, ethyl, propyl, isopropyl, butyl, isobutyl, t-butyl and pentyl groups;

(2) halogen atoms, such as the chlorine, bromine and fluorine atoms; [similar atoms may be included within substituents (d)];

(3) straight and branched chain alkoxy groups having from 1 to 5 carbon atoms, such as the methoxy, ethoxy, propoxy, isopropoxy, butoxy and pentyloxy groups; [similar groups may be included within substituents (d)]; and (4) the sulfamoyl group.

Where $R^2$, $R^4$ or $R^5$ represents a halogen atom, this is preferably a chlorine, bromine, iodine or fluorine atom, more preferably a chlorine or bromine atom.

Where $R^3$ represents a cycloalkyl group, this has from 3 to 7 ring carbon atoms, and examples include the cyclopropyl, cyclobutyl, cyclopentyl, cyclohexyl and cycloheptyl groups. $R^3$ preferably represents a cycloalkyl group containing from 3 to 5 carbon atoms.

Where $R^6$ represents an alkyl group, this is a straight or branched chain alkyl group containing from 1 to 15 carbon atoms, and examples of such groups include the methyl, ethyl, propyl, isopropyl, butyl, isobutyl, sec-butyl, t-butyl, pentyl, isopentyl, t-pentyl, hexyl, 1,3-dimethylbutyl, heptyl, octyl, 1,1,3,3-tetramethylbutyl, nonyl, decyl, undecyl, dodecyl, tridecyl, tetradecyl and pentadecyl groups. Of these, the alkyl groups having from 1 to 5 carbon atoms, examples of which are as given in relation to $R^1$, may optionally be substituted. Where the alkyl group is substituted, the substituents are selected from the group consisting of substituents (b) defined above and exemplified below.

The groups and atoms which may be included in substituents (b) are:

(1) halogen atoms, such as the chlorine, bromine and fluorine atoms;

(2) the hydroxy group;

(3) the mercapto group;

(4) dialkylamino groups in which each alkyl part is $C_1$-$C_5$ and is unsubstituted or has at least one hydroxy substituent, such as the dimethylamino, diethylamino, N-methyl-N-ethylamino, di(2-hydroxyethyl)amino, dipropylamino, N-methyl-N-propylamino, N-methyl-N-butylamino and dibutylamino groups;

(5) five- and six-membered cyclic amino groups (i.e. heterocyclic groups joined to the remainder of the molecule via the nitrogen atom), which may optionally contain a further 1 or 2 nitrogen and/or oxygen atoms in its ring and which may be unsubstituted or may be substituted with a straight or branched chain $C_1$-$C_5$ alkyl group, such as the 1-pyrrolidinyl, piperidino, morpholino and 4-methyl-1-piperazinyl groups;

(6) the phenoxy group;

(7) straight and branched chain alkoxy and hydroxyalkoxy groups containing from 1 to 5 carbon atoms, such as the methoxy, ethoxy, 2-hydroxyethoxy, hydroxymethoxy, 3-hydroxypropoxy, propoxy, isopropoxy, butoxy and pentyloxy groups;

(8) benzoyl groups which are unsubstituted or have at least one substituent selected from the group consisting of halogen atoms and straight and branched chain alkoxy groups containing from 1 to 5 carbon atoms [i.e. substituents (d)], such as the benzoyl, 4-chlorobenzoyl and 3,4,5-trimethoxybenzoyl groups;

(9) benzoyloxy groups which are unsubstituted or have at least one substituent selected from the group consisting of halogen atoms and straight and branched chain alkoxy groups containing from 1 to 5 carbon atoms [i.e. substituents (d)], such as the benzoyloxy, 4-chlorobenzoyloxy and 3,4,5-trimethoxybenzoyloxy groups; and

(10) saturated and unsaturated five- and six-membered heterocyclic acyloxy groups in which the heterocyclic ring may contain 1 or 2 nitrogen atoms, such as the pyrrole-3-carbonyloxy, pyrrolidine-3-carbonyloxy, pyrazole-4-carbonyloxy, imidazole-4-carbonyloxy, imidazolidine-4-carbonyloxy, pyridine-3-carbonyloxy (i.e. nicotinoyloxy), pyridine-4-carbonyloxy (i.e. isonicotinoyloxy), piperidine-4-carbonyloxy and pyridazine-4-carbonyloxy groups.

$R^6$ preferably represents a straight or branched chain alkyl group containing from 1 to 12 carbon atoms or a $C_1$-$C_5$ alkyl group which is substituted as defined above. Where the alkyl group is substituted, it is a straight or branched chain alkyl group containing from 1 to 5 carbon atoms and preferred examples of such substituents include: the hydroxy group; the dialkylamino group; the 5- and 6-membered heterocyclic groups; the phenoxy group; the straight and branched chain alkoxy groups containing from 1 to 3 carbon atoms; the benzoyloxy group which may be optionally substituted with a halogen atom or with a straight or branched chain alkoxy group containing from 1 to 3 carbon atoms; and the saturated and unsaturated 5- and 6-membered heterocyclic acyloxy groups containing 1 or 2 nitrogen atoms. Where the alkyl group is substituted, it is most preferably a straight or branched chain alkyl group containing from 1 to 5 carbon atoms and the substituents(s) are selected from the group consisting of the aforementioned hydroxy groups, dialkylamino groups, 5- and 6-membered heterocyclic groups, phenoxy groups, benzoyloxy groups which may optionally be substituted with a halogen atom or a straight or branched chain alkoxy group containing from 1 to 3 carbon atoms, and saturated and unsaturated 5- and 6-membered heterocyclic acyloxy groups in which the heterocyclic ring has 1 or 2 nitrogen atoms.

Where $R^6$ represents a substituted alkyl group, examples of such alkyl groups include: the halosubstituted alkyl groups, such as the chloroethyl (1-and 2-), 2,2,2-trichloroethyl, chloropropyl (1-, 2- and 3-), bromoethyl (1- and 2-) and fluoropropyl (1-, 2- and 3-) groups; hydroxy-substituted alkyl groups, such as the 2-hydroxyethyl, 3-hydroxypropyl, 2-hydroxypropyl, 4-hydroxybutyl, 2-hydroxy-1,1-dimethylethyl and 2,3-dihydroxypropyl groups; mercapto-substituted alkyl groups, such as the 2-mercaptoethyl and 3-mercaptopropyl groups; dialkylamino-substituted alkyl groups in which the alkyl group of the dialkylamino part may optionally be substituted, such as the dimethylaminoethyl, dimethylaminopropyl, dimethylaminobutyl, diethylaminoethyl, diethylaminopropyl, diethylaminobutyl, dibutylaminoethyl, dibutylaminopropyl and di(2-hydroxyethyl)aminopropyl groups; 5- and 6-membered heterocyclic-substituted alkyl groups, in which the heterocyclic part may optionally be substituted with a straight or branched chain alkyl group containing from 1 to 5 carbon atoms or which may optionally contain 1 or 2 nitrogen or oxygen atoms in the ring, such as the 2-(1-pyrrolidinyl)ethyl, 3-(1-pyrrolidinyl)propyl, 2-piperidinoethyl, 3-piperidinopropyl, 2-morpholinoethyl, 3-morpholinopropyl, 2-(4-methyl-1-piperidinyl)-ethyl and 3-(4-methyl-1-piperazinyl)propyl groups; phenoxy-substituted alkyl groups, such as the 2-phenoxyethyl, 3-phenoxypropyl and 2-phenoxyl-1-methylethyl groups; alkoxy-substituted alkyl groups, in which the alkoxy group is a straight or branched chain alkoxy group having from 1 to 5 carbon atoms, such as the ethoxymethyl, ethoxyethyl (1- and 2-) and ethoxypropyl (1-, 2- and 3-) groups; hydroxyalkoxy-substituted alkyl groups, in which the alkoxy group is a straight or branched chain alkoxy group having from 1 to 5 carbon atoms, such as the 2-(2-hydroxyethoxy)ethoxy, 2-(hydroxymethoxy)ethoxy, 2-(3-hydroxypropoxy)ethoxy and 3-(3-hydroxypropoxy)propoxy groups; benzoyl-substituted alkyl groups, in which the benzoyl group may optionally be substituted with a halogen atom or with a straight or branched chain alkoxy group containing from 1 to 5 carbon atoms, such as the benzoylmethyl, benzoylethyl (1- and 2-), benzoylpropyl (1-, 2- and 3-), 4-chlorobenzoylethyl (1- and 2-) and 3,4,5-trimethoxybenzoylmethyl groups; benzoyloxy-substituted alkyl groups, in which the benzoyl group may optionally be substituted with a halogen atom or with a straight or branched chain alkoxy group containing from 1 to 5 carbon atoms, such as the benzoyloxymethyl, benzoyloxyethyl (1- and 2-), benzoyloxypropyl (1-, 2- and 3-), 4-chlorobenzoyloxyethyl (1- and 2-), 3,4,5-trimethoxybenzoyloxyethyl (1- and 2-) and 3,4,5-trimethoxybenzoyloxyethyl (1-, 2- and 3-) groups; saturated and unsaturated 5- and 6-membered heterocyclic acyloxyalkyl groups containing 1 or 2 nitrogen atoms, such as the pyrrole-3-carbonyloxyethyl, pyrrolidine-3-carbonyloxyethyl, pyrazole-4-carbonyloxypropyl, imidazole-4-carbonyloxypropyl, imidazolidine-4-carbonyloxyethyl, pyridine-3-carbonyloxyethyl, pyridine-3-carbonyloxypropyl, pyridine-4-carbonyloxyethyl, piperidine-4-carbonyloxypropyl and pyridazine-4-carbonyloxyethyl groups.

Where $R^6$ represents an alkenyl group, this contains from 3 to 7 carbon atoms and examples of such groups include the allyl, propenyl, methallyl, 2-butenyl, 3-butenyl, 3-pentenyl, 4-hexenyl and 5-heptenyl groups; of these, those alkenyl groups containing from 3 to 5 carbon atoms are preferred.

Where $R^6$ represents an alkynyl group, this contains from 3 to 5 carbons atoms and examples of such groups include the 1-propynyl, 2-propynyl (i.e. "propargyl"), 1-butynyl, 2-butynyl, 3butynyl, 1-pentynyl, 2-pentynyl, 3-pentynyl and 4-pentynyl groups.

Where $R^6$ represents a cycloalkyl group, this may have from 3 to 10 ring carbon atoms, and examples of such groups include the cyclopropyl, cyclobutyl, cyclopentyl, cyclohexyl, cycloheptyl, cyclooctyl, cyclononyl, cyclodecyl and perhydronaphthyl groups.

Where $R^6$ represents an aralkyl group, the alkyl portion of this contains from 1 to 3 carbon atoms and the aryl portion is as generally defined above in relation to the aryl groups which may be represented by $R^6$, and may be substituted or unsubstituted as defined in relation to such aryl groups. Examples of such aralkyl groups include the benzyl, phenethyl, α-methylbenzyl, 2-phenyl-1-methylethyl, 1-phenyl-1-methylethyl, phenylpropyl (1-, 2- and 3-), 1-naphthylmethyl and 2-napthylmethyl groups. These aralkyl groups may be unsubstituted or the aryl (e.g. phenyl) part thereof may have at least one substituent selected from the group consisting of substituents (c), defined above, i.e. alkyl groups, halogen atoms and alkoxy groups; examples of these are as given in relation to the same groups which may be included in substituents (a). The alkyl side chain of the aralkyl group may instead or in addition be substituted with at least one, and preferably no more than one, hydroxy group. $R^6$ is more preferably an aralkyl group in which the alkyl part is $C_1$-$C_3$ and the aryl part is a phenyl group, which may be substituted or unsubstituted, where the substituent is at least one atom or group selected from the group consisting of: straight and branched chain alkyl groups containing from 1 to 3 carbon atoms; halogen atoms; and alkoxy groups containing from 1 to 3 carbon atoms. Examples of such substituted groups include: aralkyl groups substituted with a straight or branched chain alkyl group containing from 1 to 5 carbon atoms, such as the 4-methylbenzyl, 4-ethylbenzyl and, 3-propylbenzyl groups; halo-substituted aralkyl groups, such as the 2-chlorobenzyl, 4-chlorobenzyl, 2,6-dichlorobenzyl, b 2-fluorobenzyl, 2-fluorophenethyl, 2-bromobenzyl and 4-bromophenethyl groups; and aralkyl groups substituted with a straight or branched chain alkoxy group containing from 1 to 5 carbon atoms, such as the 4-methoxybenzyl, 3,4-dimethoxybenzyl, 3,4,5-trimethoxybenzyl, 44-ethoxybenzyl, 4-propoxybenzyl, 4-methoxyphenethyl and 3,4-dimethoxyphenethyl groups.

In the above exemplification of the groups which may be represented by $R^4$, $R^5$ and $R^6$, the examples of groups referred to apply also to those groups represented by $R^{4'}$, $R^{5'}$, $R^{6'}$, $R^{4''}$ and $R^{5''}$, so far as the case may allow..

In general, where substituents are referred to above, there is no restriction on the number of such substituents, except, as specifically explained in relation to substituents on aryl groups, those that might arise as a result of the number of substituents(s), and possibly also steric contraints. Although the exact number of substituents permissible may, therefore, vary in a manner well known to those skilled in the art, as a general rule, from 1 to 3 such substituents are preferred, except where otherwise indicated herein.

The preferred compounds of formula (Ia) of the present invention are those in which:

$R^1$ represents a hydrogen atom; a straight or branched chain alkyl group containing from 1 to 5 carbon atoms; or a carbocyclic aryl group containing from 6 to 10 carbon atoms, the aryl group being unsubstituted or having at least one substituent selected from the group consisting of substituents (a), defined and exemplified above;

$R^3$ represents a straight or branched chain alkyl group containing from 1 to 5 carbon atoms; or a cycloalkyl group containing from 3 to 7 carbon atoms;

$R^{4'}$ represents a hydrogen atom; a hydroxy group; or a straight or branched chain alkyl group containing from 1 to 5 carbon atoms;

$R_{5'}$ represents a hydrogen atom; a hydroxy group; or a straight or branched chain alkyl group containing from 1 to 5 carbon atoms;

$R^{6'}$ represents a hydrogen atom; a straight or branched chain alkyl group containing from 1 to 15 carbon atoms; a substituted straight or branched chain alkyl group containing from 1 to 5 carbon atoms and having at least one substituent selected from the group consisting of substituents (b'), defined below; a cycloalkyl group containing from 3 to 10 carbon atoms; an alkenyl group containing from 3 to 7 carbon atoms; a carbocyclic aryl group containing from 6 to 10 carbon atoms which aryl group is unsubstituted or has at least one substituent selected from the group consisting of substituents (a), defined above; or an aralkyl group in which the alkyl part is $C_1$-$C_3$ and the aryl part is a phenyl group which is unsubstituted or has at least one substituent selected from the group consisting of substituents (c), defined above;

Substituents (b')

halogen atoms, hydroxy groups, mercapto groups, dialkylamino groups in which each alkyl group has from 1 to 5 carbon atoms and is unsubstituted or has at least one hydroxy substituent, five- and six-membered heterocyclic groups which are unsubstituted or have at least one $C_1$-$C_5$ alkyl substituent and which additionally contain 0, 1 or 2 nitrogen and/or oxygen atoms in the ring, phenoxy groups, alkoxy groups containing from 1 to 5 carbon atoms, benzoyl groups which are unsubstituted or have at least one substituent selected from the group consisting of substituents (d), defined above, benzoyloxy groups which are unsubstituted or have at least one substituent selected from the group consisting of substituents (d), defined above, and heterocyclic-carbonyloxy groups in which the heterocyclic part has from 5 to 6 ring atoms of which 1 or 2 are nitrogen hetero-atoms: and pharmaceutically acceptable salts thereof.

The more preferred compounds of formula (Ia) of the present invention are those in which:

$R^1$ represents a hydrogen atom, a $C_1$-$C_3$ alkyl group, or a phenyl group, which is unsubstituted or has at least one substituent selected from the group consisting of substituents (a'), defined below;

$R^3$ represents a $C_1$-$C_3$ alkyl group or a cycloalkyl group containing from 3 to 5 carbon atoms;

$R^{4'}$ represents a hydrogen atom, a hydroxy group or a $C_1$-$C_3$ alkyl group;

$R^{5'}$ represents a hydrogen atom, a hydroxy group or $C_1$-$C_3$ alkyl group;

$R^{6'}$ represents a hydrogen atom; a $C_1$-$C_{12}$ alkyl group; a $C_1$-$C_5$ alkyl group having at least one substituent selected from the group consisting of substituents (b''), defined below; an alkynyl group containing from 3 to 5 carbon atoms; a cycloalkyl group containing from 5 to 8 carbon atoms; a phenyl group which is unsubstituted or has at least one substituent selected from the group consisting of substituents (a''), defined below; or an aralkyl group in which the alkyl part is a $C_1$-$C_3$ alkyl group and the aryl part is a phenyl group which is unsubstituted or has at least one substituent selected from the group consisting of substituents (c''), defined below;

Substituents (a')

$C_1$-$C_3$ alkyl groups, halogen atoms, $C_1$-$C_3$ alkoxy groups and sulfamonyl groups;

Substituents (b")

hydroxy groups; dialkylamino groups in which each alkyl part is $C_1$-$C_5$ and is unsubstituted or has at least one hydroxy substituent; heterocyclic groups having from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said group being unsubstituted or having at least one $C_1$-$C_5$ alkyl substituent; phenoxy groups; $C_1$-$C_3$ alkoxy groups; benzoyloxy groups which are unsubstituted or have at least one halogen and/or $C_1$-$C_3$ alkoxy substituent; and heterocyclic-carbonyloxy groups in which the heterocyclic part has from 5 to 6 ring atoms of which 1 or 2 are nitrogen hetero-atoms;

Substituents (c')

$C_1$-$C_3$ alkyl groups, halogen atoms and $C_1$-$C_3$ alkoxy groups;
and pharmaceutically acceptable salts thereof.

Still more preferred compounds of formula (Ia) of the present invention are those in which:

$R^1$ represents a hydrogen atom; a methyl group; a phenyl group which is unsubstituted or has at least one substituent selected from the group consisting of substituents (a"), defined below;

$R^3$ represents a methyl group or a cyclopropyl group;

$R^{4'}$ represents a hydrogen atom or a methyl group;

$R^{5'}$ represents a hydrogen atom or a $C_1$-$C_3$ alkyl group;

$R^{6'}$ represents a hydrogen atom; a $C_1$-$C_{12}$ alkyl group; a $C_1$-$C_5$ alkyl group having at least one substituent selected from the group consisting of substituents (b"), defined above; an alkenyl group containing from 3 to 5 carbon atoms; a cycloalkyl group containing from 5 to 8 carbon atoms; an unsubstituted phenyl group; a substituted phenyl group which has at least one substituent selected from the group consisting of halogen atoms and sulfamoyl groups; or an aralkyl group in which the alkyl part is a $C_1$-$C_3$ alkyl group and the aryl part is a phenyl group which is unsubstituted or has at least one substituent selected from the group consisting of substituents (c'), defined above;

Substituents (a")

halogen atoms and $C_1$-$C_3$ alkoxy groups;
and pharmaceutically acceptable salts thereof.

The most preferred compounds of formula (Ia) of the present invention are those in which:

$R^1$ represents a hydrogen atom or a phenyl group which is unsubstituted or has at least one substituent selected from the group consisting of $C_1$-$C_3$ alkoxy groups;

$R^3$ represents a methyl or cyclopropyl group;

$R^{4'}$ represents a hydrogen atom;

$R^{5'}$ represents a hydrogen atom or a $C_1$-$C_3$ alkyl group;

$R^{6'}$ represents a $C_1$-$C_{12}$ alkyl group; a $C_1$-$C_5$ alkyl group having at least one substituent selected from the group consisting of substituents (b'''), defined below; an alkenyl group containing from 3 to 5 carbon atoms; a cycloalkyl group containing from 5 to 8 carbon atoms; or an aralkyl group in which the alkyl part is a $C_1$-$C_3$ alkyl group and the aryl part is a phenyl group which is unsubstituted or has at least one substituent selected from the group consisting of substituents (c'), defined above;

Substituents (b''')

hydroxy groups; heterocyclic groups having from 5 to 6 ring atoms of which 1 is a nitrogen atom through which the group is attached to the remainder of the molecule and 0,1 or 2 are additional hetero-atoms selected from the group consisting of nitrogen and oxygen hetero-atoms; phenoxy groups; benzoyloxy groups which are unsubstituted or have at least one substituent selected from the group consisting of halogen atoms and $C_1$-$C_3$ alkoxy groups; and heterocyclic-carbonyloxy groups in which the heterocyclic part has from 5 to 6 ring atoms of which 1 or 2 are nitrogen hetero-atoms;
and pharmaceutically acceptable salts thereof.

The preferred compounds of formula (Ib) of the present invention are those in which:

$R^1$ represents a hydrogen atom or a phenyl group;

$R^2$ represents a hydrogen, bromine or chlorine atom;

$R^3$ represents a methyl group;

$R^{4''}$ represents a hydrogen atom, or, but only when the dotted line represents a double bond, a bromine atom;

$R^{5''}$ represents a hydrogen atom, or, but only when the dotted line represents a double bond, a bromine atom; and $R^6$ represents a $C_1$-$C_{12}$ alkyl group, a $C_1$-$C_4$ alkyl group having at least one substituent selected from the group consisting of substituents ($b^{iv}$), defined below, an allyl group, a propargyl group, a $C_5$-$C_7$ cycloalkyl group, a phenyl group, or a phenylalkyl group in which the alkyl part is $C_1$-$C_3$ and is unsubstituted and the phenyl part is unsubstituted or has at least one substituent selected from the group consisting of substituents (c"), defined below; cl Substituents ($b^{iv}$)

halogen atoms, hydroxy groups, mercapto groups, heterocyclic groups having from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said heterocyclic group being unsubstituted or having at least one $C_1$-$C_3$ alkyl substituent, benzoyloxy groups and substituted benzoyloxy group having at least one methoxy substituent;

Substituents (c")

methyl groups, chlorine atoms, fluorine atoms and methoxy groups;
and pharmaceutically acceptable salts thereof.

The more preferred compounds of formula (Ib) of the present invention are those in which:

$R^1$ represents a hydrogen atom or a phenyl group;

$R^2$ represents a hydrogen, bromine or chlorine atom;

$R^3$ represents a methyl group;

$R^{4''}$ represents a hydrogen atom;

$R^{5''}$ represents a hydrogen atom, or, but only when the dotted line represents a double bond, a bromine atom; and $R^6$ represents $C_2$-$C_4$ alkyl group, a cycloheptyl group or a phenylalkyl group in which the alkyl part is $C_1$-$C_3$ and is unsubstituted and the phenyl part is unsubstituted or has at least one substituent selected from the group consisting of methyl groups and methoxy groups; and pharmaceutically acceptable salts thereof.

The compounds of the present invention necessarily contain basic groups and can, therefore, form acid addition salts. The nature of such salts and of the acids employed to form them is not critical to the invention, provided that, where the compound is intended for use therapeutically, the salt is pharmaceutically acceptable, which, as is well known, means that it does not have a lower (or significantly lower) activity or a higher (or significantly higher) toxicity that the free base. However, where the compound is intended for other uses, e.g. as an intermediate in the preparation of other compounds, even this limitation does not apply.

Examples of acids which can form such salts include: inorganic acids, such as hydrochloric acid, hydrobromic acid, hydroiodic acid, phosphoric acid, sulfuric acid or nitric acid; organic sulfonic acids, such as methanesulfonic acid, ethanesulfonic acid, benzenesulfonic acid of p-toluenesulfonic acid; and organic carboxylic acids, such as oxalic acid, tartaric acid, citric acid, maleic acid, malonic acid, succinic acid, acetic acid, benzoic acid, mandelic acid, ascorbic acid, lactice aid, gluconic acid and malic acid.

Examples of the known class of compounds which may be used in the present invention are those compounds of formula (Ia) in which $R^1$, $R^3$, $R^{4'}$, $R^{5'}$ and $R^{6'}$ are as defined in the following Table 1. In Compound No. 43, the compound is a quaternary ammonium salt, in which the methyl iodide shown in addition to the t-butyl group in the column for $R^{6'}$ is the quaternizing compound. Examples of the new compounds of the invention are those compounds of formula (I-2) and I-3), shown below, in which $R^1$, $R^2$, $R^3$, $R^{4''}$, $R^{5''}$ and $R_6$ are as defined in Tables 2 and 3, respectively. In these Tables, the following abbreviations are used:

All allyl
Boz benzoyl
Bu butyl
iBu isobutyl
sBu sec-butyl
tBu t-butyl
Bz benzyl
Dc decyl
Ddc dodecyl
Et ethyl
Hp heptyl
cHp cycloheptyl
Hx hexyl
cHx cyclohexyl
Me methyl
Mor morpholino
Nic nicotinoyl
Oc octyl
Ph phenyl
Pip piperidyl
Piz piperazinyl
Pn pentyl
cPn cyclopentyl
iPn isopentyl
tPn t-pentyl
Pr propyl
cPr cyclopropyl
iPr isopropyl
Prg propargyl (=2-propynyl)
Pyrd pyrrolidinyl
Sam sulfamoyl

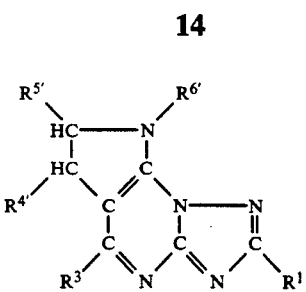

(Ia)

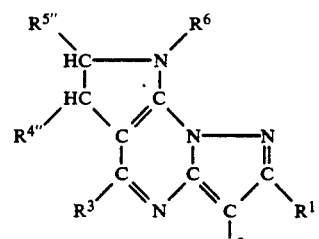

(I-2)

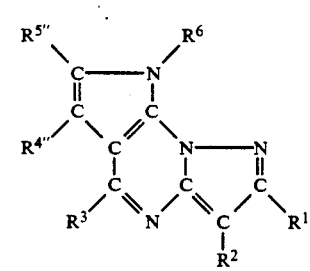

(I-3)

TABLE 1

| Cpd No. | $R^1$ | $R^3$ | $R^{4'}$ | $R^{5'}$ | $R^{6'}$ |
|---|---|---|---|---|---|
| 1-1 | H | Me | H | H | H |
| 1-2 | H | Me | H | H | Me |
| 1-3 | 4-MeOPh | Me | H | H | Me |
| 1-4 | H | Me | H | H | Et |
| 1-5 | H | Me | H | H | Pr |
| 1-6 | H | Me | H | H | iPr |
| 1-7 | Ph | Me | H | H | iPr |
| 1-8 | 4-ClPh | Me | H | H | iPr |
| 1-9 | 4-MeOPh | Me | H | H | iPr |
| 1-10 | H | Me | H | Me | iPr |
| 1-11 | H | Me | H | Et | iPr |
| 1-12 | H | cPr | H | H | iPr |
| 1-13 | H | Me | H | H | Bu |
| 1-14 | Ph | Me | H | H | Bu |
| 1-15 | H | Me | H | Me | Bu |
| 1-16 | H | Me | H | Et | Bu |
| 1-17 | H | Me | H | H | sBu |
| 1-18 | H | Me | H | H | iBu |
| 1-19 | H | Me | H | H | tBu |
| 1-20 | Me | Me | H | H | tBu |
| 1-21 | Ph | Me | H | H | tBu |
| 1-22 | 4-ClPh | Me | H | H | tBu |
| 1-23 | 4-MeOPh | Me | H | H | tBu |
| 1-24 | 3,4,5-triMeOPh | Me | H | H | tBu |
| 1-25 | H | Me | Me | H | tBu |
| 1-26 | H | Me | H | Me | tBu |
| 1-27 | H | Me | H | Et | tBu |
| 1-28 | H | cPr | H | H | tBu |
| 1-29 | H | Me | H | H | Pn |
| 1-30 | H | Me | H | H | iPn |
| 1-31 | H | Me | H | H | tPn |
| 1-32 | H | cPr | H | H | tPn |
| 1-33 | H | Me | H | H | Hx |
| 1-34 | H | Me | H | H | 1,3-diMeBu |
| 1-35 | H | Me | H | H | Hp |
| 1-36 | H | Me | H | H | 1,1,3,3-tetraMeBu |
| 1-37 | H | Me | H | H | Dc |
| 1-38 | H | Me | H | H | Ddc |
| 1-39 | H | Me | H | H | All |
| 1-40 | H | Me | H | H | cHx |

TABLE 1-continued

| Cpd No. | R¹ | R³ | R⁴' | R⁵' | R⁶' |
|---|---|---|---|---|---|
| 1-41 | H | Me | H | H | cHp |
| 1-42 | H | Me | H | H | cOc |
| 1-43 | H | Me | H | H | tBu.MeI |
| 1-44 | H | Me | H | H | Ph |
| 1-45 | H | Me | H | H | 2,6-diClPh |
| 1-46 | H | Me | H | H | 4-SamPh |
| 1-47 | H | Me | H | H | Bz |
| 1-48 | H | Me | H | H | 4-MeBz |
| 1-49 | H | Me | H | H | 4-MeOBz |
| 1-50 | H | Me | H | Me | 4-MeOBz |
| 1-51 | H | Me | H | H | 3,4-diMeOBz |
| 1-52 | H | Me | H | H | 3,4,5-triMeOBz |
| 1-53 | H | Me | H | H | 2-ClBz |
| 1-54 | H | Me | H | H | 4-ClBz |
| 1-55 | 3,4,5-triMeOPh | Me | H | H | 2-ClBz |
| 1-56 | H | Me | H | Me | 2-ClBz |
| 1-57 | H | cPr | H | H | 2-ClBz |
| 1-58 | H | Me | H | H | 2-FBz |
| 1-59 | Ph | Me | H | H | 2-FBz |
| 1-60 | H | Me | H | Me | 2-FBz |
| 1-61 | H | Me | H | Et | 2-FBz |
| 1-62 | H | Me | H | H | 1-PhEt |
| 1-63 | H | Me | H | H | 2-PhEt |
| 1-64 | H | cPr | H | H | 2-PhEt |
| 1-65 | H | Me | H | H | 2-(3,4-diMeOPh)Et |
| 1-66 | H | Me | H | H | 2-HO-1-Me-2-PhEt |
| 1-67 | Me | Me | H | H | 2-ClBz |
| 1-68 | H | Me | H | H | 2-(Et₂N)Et |
| 1-69 | H | Me | H | H | 2-(1-Pyrd)Et |
| 1-70 | H | Me | H | H | 2-(1-Pip)Et |
| 1-71 | H | Me | H | H | 2-MorEt |
| 1-72 | H | Me | H | H | 2-(4-Me-1-Piz)Et |
| 1-73 | H | Me | H | H | 3-(Me₂N)Pr |
| 1-74 | H | Me | H | H | 3-(Bu₂N)Pr |
| 1-75 | H | Me | H | H | 3-[(2-HOEt)₂N]Pr |
| 1-76 | H | Me | H | H | 3-(1-Pyrd)Pr |
| 1-77 | Me | Me | H | H | 3-(1-Pyrd)Pr |
| 1-78 | Ph | Me | H | H | 3-(1-Pyrd)Pr |
| 1-79 | 4-ClPh | Me | H | H | 3-(1-Pyrd)Pr |
| 1-80 | 4-MeOPh | Me | H | H | 3-(1-Pyrd)Pr |
| 1-81 | H | Me | H | H | 3-(1-Pip)Pr |
| 1-82 | H | Me | H | H | 3-MorPr |
| 1-83 | H | Me | H | H | 2-HOEt |
| 1-84 | H | Me | H | H | 3-HOPr |
| 1-85 | H | Me | H | H | 2-HOPr |
| 1-86 | H | Me | H | H | 2-HO-1,1-diMeEt |
| 1-87 | H | Me | H | H | 2,3-diHOPr |
| 1-88 | H | Me | H | H | 2-(2-HOEtO)Et |
| 1-89 | H | Me | H | H | 1-Me-2-PhOEt |
| 1-90 | H | Me | H | H | 2-BozEt |
| 1-91 | H | Me | H | H | 2-HSEt |
| 1-92 | H | Me | H | H | 2-ClEt |
| 1-93 | H | Me | H | H | 3-ClPr |
| 1-94 | H | Me | H | H | 2-(3,4,5-triMeOBozO)Et |
| 1-95 | H | Me | H | H | 2-NicOEt |
| 1-96 | H | Me | H | H | 3-(3,4,5-triMeOBozO)Pr |
| 1-97 | H | Me | H | H | 3-NicOPr |
| 1-98 | H | Me | OH | OH | tBu |
| 1-99 | H | Me | OH | H | tBu |
| 1-100 | H | Me | H | =O | tBu |
| 1-101 | H | Me | H | OH | tBu |

TABLE 2

| Cpd No. | R¹ | R² | R³ | R⁴'' | R⁵'' | R⁶ |
|---|---|---|---|---|---|---|
| 2-1 | H | H | Me | H | H | tBu |
| 2-2 | H | H | Me | H | H | Bz |
| 2-3 | H | Br | Me | H | H | Bz |
| 2-4 | H | Br | Me | H | H | Et |
| 2-5 | H | Br | Me | H | H | 3-MorPr |
| 2-6 | H | Br | Me | H | H | 2-HOEt |
| 2-7 | H | Br | Me | H | H | o-ClBz |
| 2-8 | H | Br | Me | H | H | 2-(3,4-diMeOPh)Et |
| 2-9 | H | Cl | Me | H | H | tBu |
| 2-10 | H | Br | Me | H | H | p-MeBz |
| 2-11 | H | Br | Me | H | H | p-MeOBz |

TABLE 2-continued

| Cpd No. | R¹ | R² | R³ | R⁴'' | R⁵'' | R⁶ |
|---|---|---|---|---|---|---|
| 2-12 | H | Br | Me | H | H | 3-HOPr |
| 2-13 | H | Cl | Me | H | H | 4-(1-Pyrd)Bu |
| 2-14 | H | Br | Me | H | H | 4-(1-Pyrd)Bu |
| 2-15 | H | H | Me | H | H | α,α-diMeBz |
| 2-16 | H | Br | Me | H | H | Pr |
| 2-17 | H | Br | Me | H | H | Bu |
| 2-18 | H | Br | Me | H | H | Ddc |
| 2-19 | H | Br | Me | H | H | cPn |
| 2-20 | H | Br | Me | H | H | cHp |
| 2-21 | H | Br | Me | H | H | 2-(3,4,5-triMeOBozO)Et |
| 2-22 | Ph | H | Me | H | H | Et |
| 2-23 | Ph | Br | Me | H | H | Et |
| 2-24 | H | Br | Me | H | H | Prg |
| 2-25 | H | Cl | Me | H | H | Prg |

TABLE 3

| Cpd No. | R¹ | R² | R³ | R⁴'' | R⁵'' | R⁶ |
|---|---|---|---|---|---|---|
| 3-1 | H | Br | Me | H | H | Me |
| 3-2 | H | Br | Me | H | Br | Me |
| 3-3 | H | Br | Me | H | H | Bu |
| 3-4 | H | Br | Me | H | H | Ddc |
| 3-5 | H | Br | Me | H | Br | Et |
| 3-6 | H | Br | cPr | H | H | Bz |
| 3-7 | H | Br | cPr | H | H | Et |
| 3-8 | H | Br | cPr | H | H | Pr |
| 3-9 | H | Br | cPr | H | H | Bu |
| 3-10 | H | Br | Me | Br | H | tBu |
| 3-11 | H | H | Me | H | H | Et |
| 3-12 | H | Cl | Me | H | H | Et |
| 3-13 | H | Br | Et | H | H | Bz |
| 3-14 | H | Cl | Pr | H | H | Bz |
| 3-15 | H | Cl | cPn | H | H | Bz |
| 3-16 | H | Br | cPn | H | H | Bz |
| 3-17 | H | Br | cPn | H | H | Et |
| 3-18 | H | Br | Me | H | H | iPr |
| 3-19 | H | Br | Me | H | H | cPn |
| 3-20 | H | Br | Me | H | H | cHx |
| 3-21 | H | Br | Me | H | H | cHp |
| 3-22 | H | Br | Me | H | H | 2-MorEt |
| 3-23 | H | Br | Me | H | H | 2-(3,4-diMeOPh)Et |
| 3-24 | H | Br | Me | H | H | All |
| 3-25 | H | Br | Me | H | H | o-FBz |
| 3-26 | H | Br | Me | H | H | 2-HOEt |
| 3-27 | H | Br | Me | H | H | 2-(3,4,5-triMeOBozO)Et |
| 3-28 | Ph | H | Me | H | H | Et |
| 3-29 | Ph | Br | Me | H | H | Et |
| 3-30 | H | Br | Me | H | H | tBu |

Of the compounds listed above, the following are preferred, that is to say Compound No. 1-3, 1-5, 1-13, 1-18, 1-19, 1-24, 1-28, 1-29, 1-30, 1-31, 1-33, 1-34, 1-35, 1-37, 1-38, 1-39, 1-41, 1-42, 1-48, 1-49, 1-53, 1-54, 1-56, 1-62, 1-63, 1-65, 1-82, 1-86, 1-89, 1-94, 1-96, 1-97, 1-98, 1-99, 2-2, 2-4, 2-9, 2-10, 2-11, 2-15, 2-20, 2-22, 3-5 and 3-28, and the following are the following more preferred, that is to say Compounds No. 1-3, 1-13, 1-18, 1-19, 1-24, 1-28, 1-29, 1-30, 1-31, 1-33, 1-34, 1-35, 1-37, 1-38, 1-39, 1-41, 1-42, 1-48, 1-49, 1-53, 1-54, 1-56, 1-62, 1-63, 1-82, 1-89, 1-97, 1-98, 1-99, 2-2, 2-4, 2-11, 2-15, 2-22, 3-5 and 3-28.

The following are the most preferred compounds:
1-13. 8-butyl-7,8-dihydro-5-methyl-6H-pyrrolo[3,2-e][1,2,4]triazolo[1,5-a]pyrimidine;
1-19. 8-t-butyl-7,8-dihydro-5-methyl-6H-pyrrolo[3,2-e][1,2,4]triazolo[1,5-a]pyrimidine;
1-28. 8-t-butyl-5-cyclopropyl-7,8-dihydro-6H-pyrrolo[3,2-e][1,2,4]triazolo[1,5-a]pyrimidine;
1-31. 7,8-dihydro-5-methyl-8-t-pentyl-6H-pyrrolo[3,2-e][1,2,4]triazolo[1,5-a]pyrimidine;

1-35. 8-heptyl-7,8-dihydro-5-methyl-6H-pyrrolo[3,2-e][1,2,4]triazolo[1,5-a]pyrimidine;

1-41. 8-cycloheptyl-7,8-dihydro-5-methyl-6H-pyrrolo[3,2-e][1,2,4]triazolo[1,5-a]pyrimidine;

1-42. 8-cyclooctyl-7,8-dihydro-5-methyl-6H-pyrrolo[3,2-e][1,2,4]triazolo[1,5-a]pyrimidine;

1-48. 7,8-dihydro-5-methyl-8-(4-methylbenzyl)-6H-pyrrolo[3,2-e][1,2,4]triazolo[1,5-a]pyrimidine;

1-49. 7,8-dihydro-8-(4-methoxybenzyl)-5-methyl-6H-pyrrolo[3,2-e][1,2,4]triazolo[1,5-a]pyrimidine;

1-54. 8-(4-chlorobenzyl)-7,8-dihydro-5-methyl-6H-pyrrolo[3,2-e][1,2,4]triazolo[1,5-a]pyrimidine;

1-62. 7,8-dihydro-5-methyl-8-(α-methylbenzyl)-6H-pyrrolo[3,2-e][1,2,4]triazolo[1,5-a]pyrimidine;

1-89. 7,8-dihydro-5-methyl-8-(1-methyl-2-phenoxyethyl)-6H-pyrrolo[3,2-e][1,2,4]triazolo[1,5-a]pyrimidine;

2-2. 8-benzyl-7,8-dihydro-5-methyl-6H-pyrazolo[1,5-a]pyrrolo[3,2-e]pyrimidine;

and pharmaceutically acceptable salts thereof.

Of the above compounds, only Compound No. 2-2 is claimed per se.

The compounds of the present invention can also form quaternary ammonium salts with suitable other compounds, especially alkyl halides in which the alkyl group contains from 1 to 4 carbon atoms, for example methyl chloride, methyl iodide, methyl bromide, ethyl chloride, ethyl iodide, ethyl bromide, propyl iodide and butyl iodide. They may be prepared by well known methods, e.g. as illustrated for the preparation of the methyl iodide salt in the Journal of Medicinal Chemistry, 23, 927–937 (1980).

All of the compounds of formula (Ia) shown above are known compounds and their properties and preparation are described in Japanese Patent Application Kokai No. Sho 51-141896, Japanese Patent Application Kokai No. Sho 52-116497, Japanese Patent Application Kokai No. Sho 53-53697, U.S. Pat. No. 4,007,189 and the Journal of Medicinal Chemistry, 23, 927–937 (1980), the disclosures whereof are incorporated herein by reference.

The new compounds of the present invention can be prepared by a variety of methods well known per se, but, in general terms, they may be prepared by the following steps:

(a) reacting a compound of formula (IV):

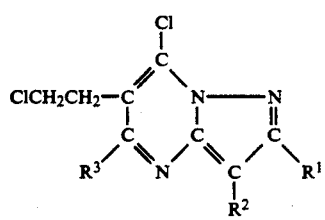

(in which $R^1$, $R^2$ and $R^3$ are as defined above) with a primary amine of formula $R^6NH_2$, to give a compound of formula (V):

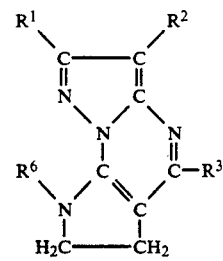

(in which $R^1$, $R^2$, $R^3$ and $R^6$ are as defined above), and, if required.

(b) dehydrogenating said compound of formula (V), to prepare a compound of formula (VI):

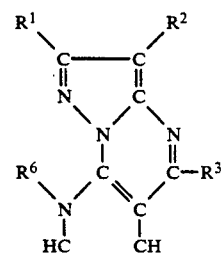

(in which $R^1$, $R^2$, $R^3$ and $R^6$ are as defined above, and the dotted line represents a carbon-carbon double bond), and, if required, (c) halogenating said compound of formula (VI) to prepare a compound of formula (VII):

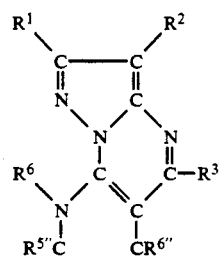

(in which $R^1$, $R^2$, $R^3$ and $R^6$ are as defined above, the dotted line represents a carbon-carbon double bond, and one of $R^{5''}$ and $R^{6''}$ represents a halogen atom and the other of $R^{5''}$ and $R^{6''}$ represents a halogen atom or a hydrogen atom), and, if required, salifying the product.

In more detail, the new compounds of the present invention can be prepared as follows:

Step (a)

This consists of a ring closure reaction by condensation of a compound of formula (VIII):

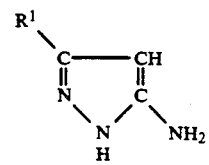

(wherein $R^1$ is as defined above) with a compound of formula (IX):

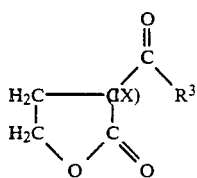

(wherein R³ is as defined above) to produce a compound of formula (X):

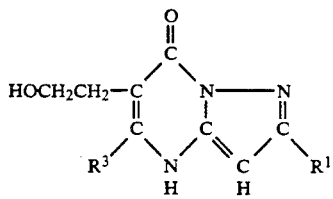

(wherein R¹ and R³ are as defined above).

The reaction is preferably effected in a solvent. There is no particular restriction on the nature of the solvent to be employed, provided that it has no adverse effect on the reaction or on the reagents involved. Examples of suitable solvents include: ethers, such as tetrahydrofuran and dioxane; aromatic hydrocarbons, such as benzene, toluene and xylene; alcohols, such as methanol and ethanol; amides, especially fatty acid amides, such as dimethylformamide and dimethylacetamide. Aromatic hydrocarbons and amides are preferred, and amides are most preferred. The amount of the lactone of formula (IX) to be employed is preferably at least equimolar, and more preferably from 1 to 2 times equimolar, with respect to the compound of formula (VIII). The reaction can take place over a wide range of temperatures, and the precise reaction temperature is not critical to the invention. In general, we find it convenient to carry out the reaction at a temperature from about 50° C. to the boiling point of the solvent employed. The time required for the reaction may also vary widely, depending on many factors, notably the reaction temperature and the nature of the reagents. However, provided that the reaction is effected under the preferred conditions outlined above, a period of from 10 minutes to 30 hours will usually suffice.

Step (b)

This step consists of the reaction of the compound of formula (X) obtained as described above with phosphorus oxychloride to produce a compound of formula (XI). The reaction can be carried out in the absence or presence of a solvent.

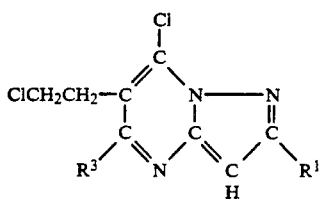

There is no particular restriction on the nature of the solvent which may be employed, provided that it has no adverse effect on the reaction or on the reagents involved. Examples of suitable solvents include: ethers, such as tetrahydrofuran or dioxane; aromatic hydrocarbons, such as benzene, toluene or xylene; and halogenated hydrocarbons, especially halogenated aliphatic hydrocarbons, such as methylene chloride, chloroform or carbon tetrachloride. It is usually preferred to conduct the reaction in the absence of a solvent. The reaction can take place over a wide range of temperatures, and the precise reaction temperature is not critical to the invention. In general, we find it convenient to carry out the reaction at a temperature from about 50° C. to the boiling point of the solvent employed. The time required for the reaction may also vary widely, depending on many factors, notably the reaction temperature and the nature of the reagents. However, provided that the reaction is effected under the preferred conditions outlined above, a period of from about 10 minutes to 10 hours will usually suffice.

Step (c)

A compound of formula (XII) can be prepared by treating the compound of formula (XI) obtained as described above with a halogenating agent, such as N-chlorosuccinimide or N-bromosuccinimide in the presence of an inert solvent.

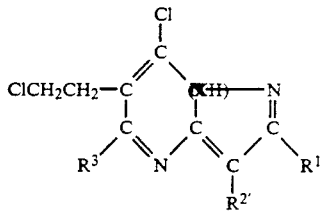

(in which R¹ and R³ are as defined above, and R²' represents a halogen atom).

There is no particular restriction on the nature of the solvent to be employed, provided that it has no adverse effect on the reaction or on the reagents involved. Examples of suitable solvents include: ethers, such as tetrahydrofuran or dioxane; aromatic hydrocarbons, such as benzene, toluene or xylene; and halogenated hydrocarbons, especially halogenated aliphatic hydrocarbons, such as methylene chloride, chloroform or carbon tetrachloride. The reaction can take place over a wide range of temperatures, and the precise reaction temperature is not critical to the invention. In general, we find it convenient to carry out the reaction at a temperature from about 0° C. to the boiling point of the solvent employed. The time required for the reaction may also vary widely, depending on many factors, notably the reaction temperature and the nature of the reagents. However, provided that the reaction is effected under the preferred conditions outlined above, a period of from about 10 minutes to 10 hours will usually suffice.

Step (d)

A compound of formula (V) can be prepared by treating the compound of formula (XI) or (XII) with a primary amine of formula R⁶NH₂ in an inert solvent and, if necessary, in the presence of a base.

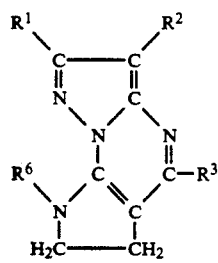

(V)

(in which $R^1$, $R^2$, $R^3$ and $R^6$ are as defined above).

The choice of the primary amine of formula $R^6NH_2$ will, of course depend solely upon the nature of the group $R^6$ which it is desired to introduce into the compound.

The nature of the base which may be employed in this reaction is not critical, provided that it does not adversely affect any other part of the molecule of the compound of formula (XI) or (XII), and examples include: organic bases such as triethylamine, pyridine or 1,8-diazabicyclo[5.4.0]-7-undecene (DBU); and alkali metal carbonates and bicarbonates, such as sodium carbonate, potassium carbonate and sodium bicarbonate.

There is no particular restriction on the nature of the solvent to be employed, provided that it has no adverse effect on the reaction or on the reagents involved. Examples of suitable solvents include: ethers, such as tetrahydrofuran or dioxane; aromatic hydrocarbons, such as benzene, toluene or xylene; halogenated hydrocarbons, especially halogenated aliphatic hydrocarbons, such as methylene chloride, chloroform or carbon tetrachloride; alcohols, such as methanol, ethanol or isopropanol; and amides, especially fatty acid amides, such as dimethylformamide or dimethylacetamide. Alcohols are preferably employed. The amount of the base to be employed may vary depending upon the nature of the primary amine employed but is usually and preferably from equimolar to 3 times equimolar, with respect to the compound of formula (XI) or (XII). The amount of the primary amine to be employed is preferably from equimolar to 10 times equimolar, also with respect to the compound of formula (XI) or (XII). The reaction can take place over a wide range of temperatures, and the precise reaction temperature is not critical to the invention. In general, we find it convenient to carry out the reaction at a temperature from about 20° C. to the boiling point of the solvent employed. The time required for the reaction may also vary widely, depending on many factors, notably the reaction temperature and the nature of the reagents. However, provided that the reaction is effected under the preferred conditions outlined above, a period of from about 10 minutes to 30 hours will usually suffice.

Step (e)

The compound of formula (V) obtained as described above can be converted to a compound of formula (VI) by dehydrogenation.

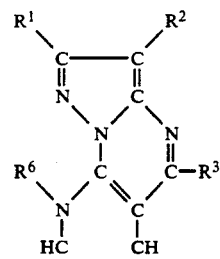

(VI)

(in which $R^1$, $R^2$, $R^3$ and $R^6$ are as defined above, and the dotted line represents a carbon-carbon double bond).

Conventional dehydrogenation agents may be used in this reaction, for example, benzoyl peroxide, metal oxides such as manganese dioxide, and dehydrogenation catalysts, such as palladium-on-carbon.

The reaction is normally and preferably effected in the presence of a solvent. There is no particular restriction on the nature of the solvent to be employed, provided that it has no adverse effect on the reaction or on the reagents involved. Examples of suitable solvents include: ethers, such as tetrahydrofuran or dioxane; aromatic hydrocarbons, such as benzene, toluene or xylene; and halogenated hydrocarbons, especially halogenated aliphatic hydrocarbons, such as methylene chloride, chloroform or carbon tetrachloride.

The reaction can take place over a wide range of temperatures, and the precise reaction temperature is not critical to the invention. In general, we find it convenient to carry out the reaction at a temperature from about 0° C. to the boiling point of the solvent employed. The time required for the reaction may also vary widely, depending on many factors, notably the reaction temperature and the nature of the reagents. However, provided that the reaction is effected under the preferred conditions outlined above, a period of from about 10 minutes to 30 hours will usually suffice.

Step (f)

A compound of formula (VII) can be prepared by treating the compound (VI) obtained as described above with a halogenating agent, such as N-chlorosuccinimide or N-bromosuccinimide in the presence of an inert solvent.

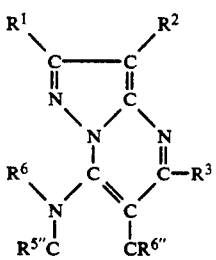

(VII)

(in which $R^1$, $R^2$, $R^3$ and $R^6$ are as defined above, the dotted line represents a carbon-carbon double bond, and one of $R^{5''}$ and $R^{6''}$ represents a halogen atom and the other of $R^{5''}$ and $R^{6''}$ represents a halogen atom or a hydrogen atom).

There is no particular restriction on the nature of the solvent to be employed, provided that it has no adverse effect on the reaction or on the reagents involved. Examples of suitable solvents include: ethers, such as tetrahydrofuran or dioxane; aromatic hydrocarbons, such as benzene, toluene or xylene; and halogenated hydrocarbons, especially halogenated aliphatic hydrocarbons, such as methylene chloride, chloroform or carbon tetrachloride. Halogenated hydrocarbons are preferred. The reaction can take place over a wide range of temperatures, and the precise reaction temperature is not critical to the invention. In general, we find it convenient to carry out the reaction at a temperature from about 0° C. to the boiling point of the solvent employed. The time required for the reaction may also vary widely, depending on many factors, notably the reaction temperature and the nature of the reagents. However, provided that the reaction is effected under the preferred conditions outlined above, a period of from about 10 minutes to 10 hours will usually suffice.

The desired product obtained as described in any of the above steps may be isolated and purified by conventional means, for example by solvent-extraction, dilution, recrystallization, or the various chromatography techniques, notably column chromatography and preparative thin layer chromatography.

The basic compounds of formula (I) may easily be converted to the corresponding acid addition salts by treatment with a suitable pharmaceutically acceptable acid. Suitable acids include: inorganic acids such as hydrochloric acid, sulfuric acid, phosphoric acid or hydrobromic acid; and organic acids such as acetic acid, oxalic acid, succinic acid, maleic acid, fumaric acid, malic acid, tartaric acid, citric acid, malonic acid, methanesulfonic acid or benzoic acid.

BIOLOGICAL ACTIVITY

Toxicity

All of the compounds of formula (I) employed in the present invention have shown low toxicity and high safety, with limited side effects. The acute toxicity ($LD_{50}$) in rats receiving 8-t-butyl-7,8-dihydro-5-methyl-6H-pyrrolo[3,2-e][1,2,4]triazolo[1,5-a]pyrimidine (Compound No. 1-19) by subcutaneous injection was not less than 100 mg/kg. The acute toxicity ($LD_{50}$) in mice receiving 8-(4-chlorobenzyl)-7,8-dihydro-5-methyl-6H-pyrrolo[3,2-e][1,2,4]triazaolo[1,5-a]pyrimidine (Compound No. 1-54), 8-(4-methoxybenzyl)-7,8-dihydro-5-methyl-6H-pyrrolo[3,2-e][1,2,4]triazolo[1,5-a]pyrimidine (Compound No. 1-49), 8-(4-methylbenzyl)-7,8-dihydro-5-methyl-6H-pyrrolo[3,2-e][1,2,4]triazolo[1,5-a]pyrimidine (Compound No. 1-48) and 8-benzyl-7,8-dihydro-5-methyl-6H-pyrazolo[1,5-a]pyrrolo[3,2-e]pyrimidine (Compound No. 2-2) by intraperitoneal injection was not less than 300 mg/kg in each case.

The compounds of the present invention may be administered in various forms, as is conventional in the art. For example, they may be administered orally in the form of tablets, capsules, granules, powders, syrups or the like or parenterally in the form of injections, drops or suppositories. The dose may vary depending upon the symptoms, age and body weight of the patient, and the nature and severity of the cachexia to be relieved, but, in general, the compounds of the invention may be administered orally in a daily dose of from about 10 to 1,000 mg for adults, either as a single dose or as divided doses, or parenterally in a single dose of from 10 to 500 mg by hypodermic, intramuscular or intravenous injection.

The enhancement index employed herein is calculated as follows:

Induction, suppression and assay of the lipoprotein lipase are carried out according to the methods reported by Beutler et al. [J. Immunol., 135, 3972-2977(1985)]. The differentiated adipocytes (3T3-L1) are incubated for 18 hours in the presence of a 2% (v/v) dispersion of serum taken from rabbits, to which the endotoxin had previously been intravenously administered. The serum obtained is named TNS. The enzyme activity of the adipocytes is determined after the incubation. The activity so determined corresponds to 5-15% of that activity which is determined after incubation in the presence of the serum taken from rabbits which had not been administered the endotoxin.

When the compounds employed in this invention are added in an amount of from 0.1 to 100 microgram/ml to the adipocyte culture and the culture is incubated for 18 hours in the presence of 2% of TNS, the enzyme activity is enhanced and is higher than the activity determined in the absence of the compound.

The enhancement index of the lipoprotein lipase-
=A/B, where:

A: Heparin releasable lipoprotein lipase activity of the adipocyte after 18 hours incubation in the presence of TNS and the compounds tested.

B: Heparin releasable lipoprotein lipase activity of the adipocyte after 18 hours incubation in the presence of TNS and in the absence of the compounds.

The enhancement index of each compound is calculated at the concentration to show the highest efficacy.

TNS is prepared according to the methods reported by Ostrove et al. [J. M. Ostrove et al.; Proceeding of the Society for Experimental Biology and Medicine, 160, 354-358(1979)]. Forty mg per head of lyophilized hypodermic BCG vaccine (Japan BCG Ind., Japan) are injected into the marginal ear vein of female New Zealand white rabbits. Two weeks later, these rabbits are injected with 10 μg per head of the lipopolysaccharide (derived from *E. coli* 0127:B8, purchased from Difco Lab., USA) via the ear vein, and the animals are bled 1.5-2 hours later after the challenge. The blood obtained is incubated for 2 hours at 37° C. to allow clotting, and then centrifuged at 3,000 rpm for 10 minutes to obtain a serum without debris. The serum obtained is incubated at 56° C. for 30 minutes and is then sterilized by filtration through a 0.22 μm Millex-GS filter (Millipore Co., USA). The filtrate obtained is called TNS.

The activity of the compounds of the present invention is illustrated by the following experiments.

EXPERIMENT 1

Restoration of Lipoprotein Lipase in Cultured Adipocytes

The induction, suppression and determination of lipoprotein lipase were carried out according to the methods reported by Beutler et al. as described above [J. Immunol., 135, 3972-3977(1985)]. The fact that the restoration of lipolytic activity by the compounds of the present invention is due to the enhancement of the lipoprotein lipase, was ascertained as follows.

It is known that 1.0M of NaCl added to the reaction mixture for assay inhibits the activity of the lipoprotein lipase but does not inhibit both hepatic triglyceride lipase [A. Bensadoun et al.; J. Biol. Chem., 249, 2220-2227(1974), J. C. LaRosa et al.; J. Lipid Res., 13, 356-363(1972)]. The lipase activity of adipocytes incubated with the compounds of the present invention was clearly detected in the reaction mixture containing 0.1M NaCl, but not in the reaction mixture containing 1.0M NaCl.

In addition, the lipase activity of the adipocytes (3T3-L1) incubated with the compounds of the present invention was not affected by 500 μM of chloropromazine, a specific inhibitor for the lysosomal lipase [G. L. Jansen et al.; J. Biol. Chem., 255, 11141-11148(1980)]. Accordingly, it is concluded that the lipolytic activity restored by the compounds is due to lipoprotein lipase, when the activity is suppressed by TNS.

The remarkable restoration of the lipoprotein lipase by the compounds in the invention, is shown in Table 4.

The compounds of the present invention are regarded as particularly useful as they each have an enhancement index of at least 2.

TABLE 4

| Compound No. | Dosage (μg/ml) | Enhancement of lipoprotein lipase |
|---|---|---|
| 1-3 | 10 | 3.0 |
| 1-5 | 100 | 4.7 |
| 1-13 | 10 | 2.5 |
| 1-18 | 10 | 2.2 |
| 1-19 | 10 | 8.5 |
| 1-24 | 1.0 | 2.0 |
| 1-28 | 10 | 9.5 |
| 1-29 | 10 | 5.2 |
| 1-30 | 10 | 10 |
| 1-31 | 10 | 2.8 |
| 1-33 | 10 | 5.6 |
| 1-34 | 10 | 8.5 |
| 1-35 | 10 | 6.9 |
| 1-37 | 10 | 4.9 |
| 1-38 | 10 | 10 |
| 1-39 | 1.0 | 6.1 |
| 1-41 | 10 | 10 |
| 1-42 | 10 | 27 |
| 1-48 | 10 | 12 |
| 1-49 | 10 | 12 |
| 1-53 | 10 | 3.0 |
| 1-54 | 10 | 9.8 |
| 1-56 | 10 | 4.0 |
| 1-62 | 10 | 8.0 |
| 1-63 | 10 | 6.0 |
| 1-65 | 100 | 5.4 |
| 1-82 | 10 | 9.0 |
| 1-86 | 100 | 3.0 |
| 1-89 | 10 | 8.1 |
| 1-94 | 100 | 6.0 |
| 1-96 | 100 | 19 |
| 1-97 | 10 | 16 |
| 1-98 | 10 | 3.2 |
| 1-99 | 10 | 2.6 |
| 2-2 | 10 | 11.2 |
| 2-4 | 10 | 3.4 |
| 2-9 | 1.0 | 2.0 |
| 2-10 | 1.0 | 2.0 |
| 2-11 | 0.1 | 3.7 |
| 2-15 | 1.0 | 4.0 |
| 2-20 | 10 | 2.7 |
| 2-22 | 10 | 3.7 |
| 3-5 | 1.0 | 4.8 |
| 3-28 | 1.0 | 3.7 |

EXPERIMENT 2

The Enhancement of Lipoprotein Lipase Activity in Mice

Female mice (Balb/c, 10 weeks old, n=6, i.e. the number in each test group was 6) were injected with 9 mg/kg of the test compound (Compound No. 1-19) via the tail vein. Twenty one hours later, the activities of the plasma lipoprotein lipase were determined according to Vlassara's method [Horm. Metabol. Res., 18, 698-703(1986)].

Activities of the plasma lipoprotein lipase in control mice receiving physiological saline were expressed as 100 and the relative value is shown in the following Table 5.

TABLE 5

|  | Group receiving saline (n = 6) | Group receiving the test compound (n = 6) |
|---|---|---|
| Relative activity of the lipoprotein lipase | 100 ± 13.5* | 120 ± 10.6* |

*mean ± standard deviation.

A significant difference between the two groups was observed (p<0.05).

As indicated above, the lipoprotein lipase activity was increased to 120% of that of the control, when the mice were administrated the test compound (Compound No. 1-19).

EXPERIMENT 3

The effects on Improving Cachexia and Increasing Life-Span of Tumor Bearing Mice A mouse cachexia model was made by inoculating $6 \times 10^5$ viable tumor cells, adenocarcinoma C-12G, subcutaneously into the right axillary region of a $CSF_1$ mouse (8-9 weeks old, female weighing 21-24 g, n=10). The viable tumor cells were counted under a microscope after staining them with 0.4% of trypan blue (Sigma Co.).

The growth of this kind of tumor, inoculated subcutaneously, causes a marked weight loss (the weight losses of mice 16-17 days after tumor inoculation were 4.0-4.5 g), piloerection and depression of emotion and finally death.

Compound No. 1-19 (hereafter called the test compound) was suspended in saline containing 0.5% CMC (carboxymethyl cellulose) at a concentration of 4 mg/ml. The suspension was administrated orally to mice on days 1-4, 7-11, 14-24 (20 times in total) after the tumor inoculation. The status of the mice, such as weight loss, piloerection, depression of emotion and increase in life-span, was observed.

On the other hand, for a control group of mice, saline solution containing 0.5% of CMC was given orally. As a result of the oral administration of the test compound, extensive improvements in weight, hair retention and emotion were observed in the mice. As shown in Table 6 it was also found that the test compound produced an increase in life-span (ILS) comparing with control mice.

TABLE 6

|  | Dose (mg/kg/day) | Median Survival time (day) | Increase in life-span (%) |
|---|---|---|---|
| Control | — | 28.0 | — |
| Compound 1-19 | 40 | 40.5 | 45 |

$$ILS \% = \left( \frac{\text{Median survival time of sample treated mice}}{\text{Median survival time of control mice}} - 1 \right) \times 100$$

In the above, the median survival times were measured in days.

The preparation of pharmaceutical compositions according to the present invention is illustrated in the following Formulations.

| FORMULATION 1 | |
|---|---|
| Tablets | |
| 1) 8-t-Butyl-7,8-dihydro-5-methyl-6H-pyrrolo[3,2-e][1,2,4]triazolo-[1,5-a]pyrimidine (Compound No. 1-19) | 200 g |
| 2) Sodium pyrosulfate | 5 |
| 3) Aerosil 200 | 5 |
| 4) Magnesium stearate | 5 |
| 5) Lactose | 495 |
| 6) Cornstarch | 154 |
| 7) Avicel | 123 |
| 8) HPC (L) | 10 |
| | 997 g |

A mixture of the powdered compounds 1 to 4 was added to granules prepared from a mixture of the compounds 5 to 8, and the mixture was compressed using a tablet machine to make a tablet containing 100 mg per tablet. The tablet may be sugar-coated, where necessary.

| FORMULATION 2 | |
|---|---|
| Capsules | |
| 1) 8-t-Butyl-7,8-dihydro-5-methyl-6H-pyrrolo[3,2-e][1,2,4]triazolo-[1,5-a]pyrimidine (Compound No. 1-19) | 200 g |
| 2) Calcium phosphate, dibasic | 200 |
| 3) Aluminum silicate | 345 |
| 4) Crystalline Cellulose | 250 |
| 5) Magnesium stearate | 2 |
| | 997 g |

The above compounds 1 to 5 were mixed and pulverized, and then mixed well through a sieve. Then, the mixture was made into capsules containing 200 mg per capsule by a conventional method.

The preparation of the new compounds of the present invention is illustrated by the following Examples.

EXAMPLE 1

6-(2-Hydroxyethyl)-5-methylpyrazolo[1,5-a]pyrimidin-7(4H)-one

A solution of 49.86 g (0.6 mole) of 3-aminopyrazole and 84.56 g (0.66 mole) of α-acetyl-γ-butyrolactone dissolved in 60 ml of N,N-dimethylformamide was heated under reflux for 2 hours. At the end of this time, the reaction mixture was cooled to room temperature, after which 100 ml of ethanol was added to it and the precipitated crystals were collected by filtration. They were then washed with ethanol to afford 104.9 g (yield 90%) of the title compound as prisms, melting at 225°–226° C.

$^1$H-Nuclear Magnetic Resonance Spectrum (hexadeuterated dimethyl sulfoxide) δ ppm:
2.35 (3H, singlet);
2.42–2.82 (2H, multiplet);
3.20–3.70 (2H, multiplet);
4.58 (1H, triplet, J=6 Hz);
6.03 (1H, doublet, J=2 Hz);
7.81 (1H, doublet, J=2 Hz);
12.07 (1H, broad);
12.48 (1H, broad).

EXAMPLE 2

Following a similar procedure to that described in Example 1, 1.72 g (yield 63.9%) of 6-(2-hydroxyethyl)-5-methyl-2-phenylpyrazolo[1,5-a]pyrimidin-7-(4H)-one was prepared as a light brown powder, melting at 284° C. (with decomposition).

EXAMPLE 3

7-Chloro-6-(2-chloroethyl)-5-methylpyrazolo[1,5-a]-pyrimidine

A mixture of 5.80 g (30 mmoles) of 6-(2-hydroxyethyl)-5-methylpyrazolo[1,5-a]pyrimidin-7(4H)-one (prepared as described in Example 1) and 30 ml of phosphorous oxychloride was heated under reflux for 4 hours, with stirring. The reaction mixture was then poured into ice-water and extracted with chloroform. The extract was washed with water and dried over anhydrous magnesium sulfate, after which it was concentrated by evaporation under reduced pressure. The residue was purified by column chromatography through silica gel (eluted with chloroform) and recrystallized from hexane, to afford 5.5 g (yield 80%) of the title compound as light yellow prisms, melting at 87°–88° C.

$^1$H-Nuclear Magnetic Resonance Spectrum (CDCl$_3$) δ ppm:
2.71 (3H, singlet);
3.18–3.50 (2H, multiplet);
3.60–3.97 (2H, multiplet);
6.68 (1H, doublet, J=2.5 Hz);
8.17 (1H, doublet, J=2.5 Hz).

EXAMPLE 4

Following a similar procedure to that described in Example 3, 1.77 g (yield 57.8%) of 7-chloro-6-(2-chloroethyl)-5-methyl-2-phenylpyrazolo[1,5-a]pyrimidine was prepared as yellow needles, melting at 147°–149° C.

EXAMPLE 5

3-Bromo-7-chloro-6-(2-chloroethyl)-5-methyl-pyrazolo[1,5-a]-pyrimidine 2.35 g (13.2 mmoles) of N-bromosuccinimide was added to a solution of 2.53 g (11 mmoles) of 7-chloro-6-(2-chloroethyl)-5-methylpyrazolo[1,5-a]pyrimidine (prepared as described in Example 3) dissolved in 20 ml of chloroform, and the mixture was heated under reflux, with stirring, for 30 minutes. At the end of this time, the reaction mixture was washed with a 2N aqueous solution of potassium hydroxide and then with water, after which it was dried over anhydrous sodium sulfate and then concentrated by evaporation under reduced pressure. The residue was purified by column chromatography through alumina (eluted with chloroform) and recrystallized from diisopropyl ether to afford 3.33 g (yield 98%) of the title compound as colorless needles, melting at 128.5°–129.5° C.

$^1$H-Nuclear Magnetic Resonance Spectrum (CDCl$_3$) δ ppm:
2.77 (3H, singlet);
3.20–3.50 (2H, multiplet);
3.63–3.97 (2H, multiplet);
8.18 (1H, singlet).

EXAMPLE 6

3,7-Dichloro-6-(2-chloroethyl)-5-methylpyrazolo[1,5-a]-pyrimidine 1.60 g (12 mmoles) of N-chlorosuccinimide were added to a solution of 2.30 g (10 mmoles) of 7-chloro-6-(2-chloroethyl)-5-methylpyrazolo[1.5-a]pyrimidine (prepared as described in Example 3) in 10 ml of chloroform, and the resulting mixture was heated under reflux, with stirring, for one hour. At the end of this time, the reaction mixture was washed with a 2N aqueous solution of potassium hydroxide and then with water, after which it was dried over anhydrous sodium sulfate and then concentrated by evaporation under reduced pressure. The residue was purified by column chromatography through alumina (eluted with chloroform) and recrystallized from diisopropyl ether to afford 1.56 g (yield 59%) of the title compound as light yellow needles, melting at 115°–117° C.

$^1$H-Nuclear Magnetic Resonance Spectrum (CDCl$_3$) δ ppm:
2.77 (3H, singlet);
3.13–3.52 (2H, multiplet);
3.63–3.98 (2H, multiplet);
8.18 (1H, singlet).

EXAMPLE 7

8-Benzyl-7,8-dihydro-5-methyl-6H-pyrazolo[1,5-a]pyrrolo[3,2-e]pyrimidine

A solution of 1.15 g (5 mmoles) of 7-chloro-6-(2-chloroethyl)-5-methylpyrazolo[1,5-a]pyrimidine (prepared as described in Example 3), 643 mg (6 mmoles) of benzylamine and 2 ml of triethylamine dissolved in 5 ml of isopropanol was heated under reflux for 7 hours, with stirring. The reaction mixture was then poured into water and extracted with ethyl acetate. The organic layer was extracted with 5% by volume aqueous sulfuric acid, and the extract was made basic by the addition of sodium carbonate. The crystals which precipitated were collected by filtration and washed with water. They were then purified by column chromatography through silica gel (eluted with chloroform) and recrystallized from a mixture of ethyl acetate and chloroform, to afford 788 mg (yield 60%) of the title compound as colorless needles, melting at 130°–130.5° C.

$^1$H-Nuclear Magnetic Resonance Spectrum (CDCl$_3$) δ ppm:
2.38 (3H, singlet);
2.80–3.25 (2H, multiplet);
3.40–3.81 (2H, multiplet);
6.37 (1H, doublet, J=2.5 Hz);
8.01 (1H, doublet, J=2.5 Hz).

EXAMPLE 8

Following a similar procedure to that described in Example 7, 956 mg (yield 68%) of 3-bromo-7,8-dihydro-8-ethyl-5-methyl-6H-pyrazolo[1,5-a]pyrrolo[3,2-e]pyrimidine were prepared as light yellow needles, melting at 163°–165° C.

$^1$H-Nuclear Magnetic Resonance Spectrum (CDCl$_3$) δ ppm:
2.38 (3H, singlet);
3.05 (2H, triplet, J=9 Hz);
3.82 (2H, triplet, J=9 Hz);
7.93 (1H, singlet).

EXAMPLE 9

Following a similar procedure to that described in Example 7, 1.296 g (yield 49%) of 8-(t-butyl)-3-chloro-7,8-dihydro-5-methyl-6H-pyrazolo[1,5-a]pyrrolo[3,2-e]pyrimidine was prepared as light yellow prisms, melting at 132.5°–134° C.

$^1$H-Nuclear Magnetic Resonance Spectrum (CDCl$_3$) δ ppm:
2.40 (3H, singlet);
2.97 (2H, triplet, J=9 Hz);
4.00 (2H, triplet, J=9 Hz);
7.93 (1H, singlet).

EXAMPLE 10

Following a similar procedure to that described in Example 7, 1.366 g (yield 73%) of 3-bromo-7,8-dihydro-8-(4-methoxybenzyl)-5-methyl-6H-pyrazolo[1,5-a]pyrrolo[3,2-e]pyrimidine was prepared as light yellow needles, melting at 147°–149° C.

$^1$H-Nuclear Magnetic Resonance Spectrum (CDCl$_3$) δ ppm:
2.38 (3H, singlet);
3.02 (2H, multiplet);
3.68 (2H, multiplet);
8.00 (1H, singlet).

EXAMPLE 11

Following a similar procedure to that described in Example 7, 1.70 g (yield 32.4%) of 3-bromo-8-cycloheptyl-7,8-dihydro-5-methyl-6H-pyrazolo[1,5-a]pyrrolo[3,2-e]pyrimidine was prepared as colorless needles, melting at 184°–185° C.

$^1$H-Nuclear Magnetic Resonance Spectrum (CDCl$_3$) δ ppm:
2.36 (3H, singlet);
3.02 (2H, multiplet);
3.82 (2H, multiplet);
7.90 (1H, singlet).

EXAMPLE 12

Following a similar procedure to that described in Example 7, 2.57 g (yield 61.6%) of 8-ethyl-7,8-dihydro-5-methyl-2-phenyl-6H-pyrazolo[1,5-a]pyrrolo[3,2-e]pyrimidine was prepared as light yellow needles, melting at 197°–198.5° C.

EXAMPLE 13

3-bromo-8-ethyl-5-methyl-8H-pyrazolo[1,5-a]pyrrolo[3,2-e]pyrimidine 2.16 g (8.92 mmoles) of benzoyl peroxide were added to a solution of 2.50 g (8.89 mmoles) of 3-bromo-7,8-dihydro-8-ethyl-5-methyl-6H-pyrazolo[1,5-a]pyrrolo[3,2-e]pyrimidine (prepared as described in Example 8) dissolved in 30 ml of benzene, and the mixture was stirred for 2 hours. At the end of this time, the reaction mixture was washed with a 5% v/v aqueous solution of sodium bicarbonate and then with water, after which it was dried over anhydrous sodium sulfate and then concentrated by evaporation under reduced pressure. The residue was purified by column chromatography through silica gel (eluted with chloroform) and recrystallized from diisopropyl ether to afford 1.019 g (yield 41%) of the title compound as light yellow needles, melting at 113°–114° C.

$^1$H-Nuclear Magnetic Resonance Spectrum (CDCl$_3$) δ ppm:
2.78 (3H, singlet);
6.61 (1H, doublet, J=3.5 Hz);
6.68 (1H, doublet, J=3.5 Hz);
8.02 (1H, singlet).

EXAMPLE 14

Following a similar procedure to that described in Example 13, 1.10 g (yield 73.8%) of 8-ethyl-5-methyl-2-phenyl-8H-pyrazolo[1,5-a]pyrrolo[3,2-e]pyrimidine was prepared as light yellow prisms, melting at 142°–143.5° C.

EXAMPLE 15

3,7-Dibromo-8-ethyl-5-methyl-8H-pyrazolo[1,5-a]pyrrolo[3,2-e]pyrimidine

N-bromosuccinimide was added at room temperature to a solution of 1.675 g (6 mmoles) of 3-bromo-8-ethyl-5-methyl-8H-pyrazolo[1,5-a]pyrrolo[3,2-e]pyrimidine (prepared as described in Example 13) dissolved in 12 ml of chloroform, and the mixture was stirred for 2 hours. At the end of this time, the reaction mixture was washed with a 2N aqueous solution of potassium hydroxide and then with water, after which it was dried over anhydrous sodium sulfate and then concentrated by evaporation under reduced pressure. The residue was purified by column chromatography through silica gel (eluted with chloroform) and recrystallized from ethyl acetate to afford 1.72 g (yield 80%) of the title compound as colorless needles, melting at 135°–137° C.

$^1$H-Nuclear Magnetic Resonance Spectrum (CDCl$_3$) δppm:
2.72 (3H, singlet);
6.68 (1H, singlet);
7.98 (1H, singlet).

We claim:

1. A method of treating or alleviating the effects of cachexia comprising administering to a mammal an effective amount of an active agent sufficient to alleviate at least one effect selected from the group consisting of weight loss, depression of emotion, depression of appetite, disorder of lipid metabolism, piloerection, decreased response to chemotherapy and decreased response to radiotherapy, wherein said active agent is at least one enhancer of the activity of lipoprotein lipase selected from the group consisting of compounds of formula (Ib):

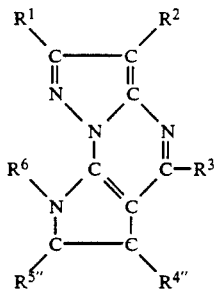

in which:
the dotted line represents a carbon-carbon double bond or a carbon-carbon single bond and, if necessary, a hydrogen atom at one or both of the carbon atoms which the bond links;
$R^1$ represents a hydrogen atom, a $C_1$–$C_5$ alkyl group or a $C_6$–$C_{10}$ carbocyclic aryl group which is unsubstituted or has at least one substituent selected from the group consisting of substituents (a), defined below;
$R^2$ represents a hydrogen atom or a halogen atom;
$R^3$ represents a $C_1$–$C_5$ alkyl group or a $C_3$–$C_7$ cycloalkyl group;
$R^{4'}$ represents a hydrogen atom, or, but only when the dotted line represents a double bond, a hydrogen atom or a halogen atom; and
$R^{5'}$ represents a hydrogen atom, or, but only when the dotted line represents a double bond, a hydrogen atom or a halogen atom;
$R^6$ represents a hydrogen atom, a $C_1$–$C_{15}$ alkyl group, a $C_1$–$C_5$ alkyl group having at least one substituent selected from the group consisting of substituents (b), defined below, a $C_3$–$C_7$ alkenyl group, a $C_3$–$C_5$ alkynyl group, a $C_3$–$C_{10}$ cycloalkyl group, a $C_6$–$C_{10}$ carbocyclic aryl group which is unsubstituted or has at least one substituent selected from the group consisting of substituents (a), defined below, or an aralkyl group in which the alkyl part is $C_1$–$C_3$ and is unsubstituted or has at least one hydroxy substituent, and the aryl part is a $C_6$–$C_{10}$ carbocyclic aryl group which is unsubstituted or has at least one substituent selected from the group consisting of substituents (c), defined below;

substituents (a):
$C_1$–$C_5$ alkyl groups, halogen atoms, $C_1$–$C_5$ alkoxy groups and sulfamoyl groups;

substituents (b):
halogen atoms, hydroxy groups, mercapto groups, dialkylamino groups in which each alkyl part is $C_1$–$C_5$ and is unsubstituted or has at least one hydroxy substituent, heterocyclic groups as defined below, phenoxy groups, $C_1$–$C_5$ alkoxy groups, $C_1$–$C_5$ hydroxyalkoxy groups, benzoyl groups, substituted benzoyl groups having at least one substituent selected from the group consisting of substituents (d), defined below, benzoyloxy groups, substituted benzoyloxy groups having at least one substituent selected from the group consisting of substituents (d), defined below, and heterocycliccarbonyloxy groups in which the heterocyclic part has from 5 to 6 ring atoms of which 1 or 2 are nitrogen hetero-atoms;

substituents (c):
$C_1$–$C_5$ alkyl groups, halogen atoms and $C_1$–$C_5$ alkoxy groups;

substituents (d):
halogen atoms and $C_1$–$C_5$ alkoxy groups;
said heterocyclic groups have from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said group being unsubstituted or having at least one $C_1$–$C_5$ alkyl substituent;
and pharmaceutically acceptable salts thereof.

2. The method of claim 1, in which:
$R^1$ represents a hydrogen atom or a phenyl group;
$R^2$ represents a hydrogen, bromine or chlorine atom;
$R^3$ represents a methyl group;
$R^{4''}$ represents a hydrogen atom, or, but only when the dotted line represents a double bond, a bromine atom;
$R^{5''}$ represents a hydrogen atom, or, but only when the dotted line represents a double bond, a bromine atom; and
$R^6$ represents a $C_1$–$C_{12}$ alkyl group, a $C_1$–$C_4$ alkyl group having at least one substituent selected from the group consisting of substituents (b$^{iv}$), defined below, an allyl group, a propargyl group, a $C_5$–$C_7$ cycloalkyl group, a phenyl group, or a phenylalkyl group in which the alkyl part is $C_1$–$C_3$ and is unsubstituted and the phenyl part is unsubstituted or has at least one substituent selected from the group consisting of substituents (c''), defined below;

substituents (b^{iv}):
halogen atoms, hydroxy groups, mercapto groups, heterocyclic groups having from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said heterocyclic group being unsubstituted or having at least one $C_1$-$C_3$ alkyl substituent, benzoyloxy groups and substituted benzoyloxy groups having at least one methoxy substituent;

substituents (c''):
methyl groups, chlorine atoms, fluorine atoms and methoxy groups.

3. The method of claim 1, in which:
$R^1$ represents a hydrogen atom or a phenyl group;
$R^2$ represents a hydrogen, bromine or chlorine atom;
$R^3$ represents a methyl group;
$R^{4''}$ represents a hydrogen atom;
$R^{5''}$ represents a hydrogen atom, or, but only when the dotted line represents a double bond, a bromine atom; and
$R^6$ represents a $C_2$-$C_4$ alkyl group, a cycloheptyl group or a phenylalkyl group in which the alkyl part is $C_1$-$C_3$ and is unsubstituted and the phenyl part is unsubstituted or has at least one substituent selected from the group consisting of methyl groups and methoxy groups.

4. A compound of formula (Ib):

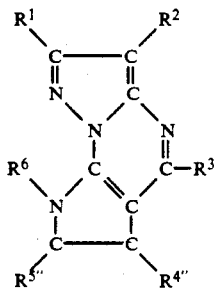

in which:
the dotted line represents a carbon-carbon double bond or a carbon-carbon single bond and, if necessary a hydrogen atom at one or both of the carbon atoms which the bond links;
$R^1$ represents a hydrogen atom, a $C_1$-$C_5$ alkyl group or a $C_6$-$C_{10}$ carbocyclic aryl group which is unsubstituted or has at least one substituent selected from the group consisting of substituents (a), defined below;
$R^2$ represents a hydrogen atom or a halogen atom;
$R^3$ represents a $C_1$-$C_5$ alkyl group or a $C_3$-$C_7$ cycloalkyl group;
$R^{4''}$ represents a hydrogen atom, or, but only when the dotted line represents a double bond, a hydrogen atom or a halogen atom;
$R^{5''}$ represents a hydrogen atom, or, but only when the dotted line represents a double bond, a hydrogen atom or a halogen atom; and
$R^6$ represents a hydrogen atom, a $C_1$-$C_{15}$ alkyl group, a $C_1$-$C_5$ alkyl group having at least one substituent selected from the group consisting of substituents (b), defined below, a $C_3$-$C_7$ alkenyl group, a $C_3$-$C_5$ alkynyl group, a $C_3$-$C_{10}$ cycloalkyl group, a $C_6$-$C_{10}$ carbocyclic aryl group which is unsubstituted or has at least one substituent selected from the group consisting of substituents (a), defined below, or an aralkyl group in which the alkyl part is $C_1$-$C_3$ and is unsubstituted or has at least one hydroxy substituent, and the aryl part is a $C_6$-$C_{10}$ carbocyclic aryl group which is unsubstituted or has at least one substituent selected from the group consisting of substituents (c), defined below;

substituents (a):
$C_1$-$C_5$ alkyl groups, halogen atoms, $C_1$-$C_5$ alkoxy groups and sulfamoyl groups;

substituents (b):
halogen atoms, hydroxy groups, mercapto groups, dialkylamino groups in which each alkyl part is $C_1$-$C_5$ and is unsubstituted or has at least one hydroxy substituent, heterocyclic groups as defined below, phenoxy groups, $C_1$-$C_5$ alkoxy groups, $C_1$-$C_5$ hydroxyalkoxy groups, benzoyl groups, substituted benzoyl groups having at least one substituent selected from the group consisting of substituents (d), defined below, benzoyloxy groups, substituted benzoyloxy groups having at least one substituent selected from the group consisting of substituents (d), defined below, and heterocycliccarbonyloxy groups in which the heterocyclic part has from 5 to 6 ring atoms of which 1 or 2 are nitrogen hetero-atoms;

substituents (c):
$C_1$-$C_5$ alkyl groups, halogen atoms and $C_1$-$C_5$ alkoxy groups;

substituents (d):
halogen atoms and $C_1$-$C_5$ alkoxy groups;

said heterocyclic groups have from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said group being unsubstituted or having at least one $C_1$-$C_5$ alkyl substituent;

and pharmaceutically acceptable salts thereof.

5. The compound of claim 4, in which:
$R^1$ represents a hydrogen atom or a phenyl group;
$R^2$ represents a hydrogen, bromine or chlorine atom;
$R^3$ represents a methyl group;
$R^{4''}$ represents a hydrogen atom, or, but only when the dotted line represents a double bond, a bromine atom;
$R^{5''}$ represents a hydrogen atom, or, but only when the dotted line represents a double bond, a bromine atom; and
$R^6$ represents a $C_1$-$C_{12}$ alkyl group, a $C_1$-$C_4$ alkyl group having at least one substituent selected from the group consisting of substituents (b^{iv}), defined below, an allyl group, a propargyl group, a $C_5$-$C_7$ cycloalkyl group, a phenyl group, or a phenylalkyl group in which the alkyl part is $C_1$-$C_3$ and is unsubstituted and the phenyl part is unsubstituted or has at least one substituent selected from the group consisting of substituents (c''), defined below;

substituents (b^{iv}):
halogen atoms, hydroxy groups, mercapto groups, heterocyclic groups having from 5 to 6 ring atoms of which 1 is a nitrogen atom through which the group is attached to the remainder of the molecule and 0, 1 or 2 are additional hetero-atoms selected from the group consisting of nitrogen and oxygen hetero-atoms, said heterocyclic group being unsubstituted or having at least one $C_1$-$C_3$ alkyl substituent, benzoyloxy groups and substituted benzoyloxy groups having at least one methoxy substituent;

substituents (c''):

methyl groups, chlorine atoms, fluorine atoms and methoxy groups.

6. The compound of claim 4, in which:

$R^1$ represents a hydrogen atom or a phenyl group;

$R^2$ represents a hydrogen, bromine or chlorine atom;

$R^3$ represents a methyl group;

$R^{4''}$ represents a hydrogen atom;

$R^{5''}$ represents a hydrogen atom, or, but only when the dotted line represents a double bond, a bromine atom; and $R^6$ represents a $C_2$-$C_4$ alkyl group, a cycloheptyl group or a phenylalkyl group in which the alkyl part is $C_1$-$C_3$ and is unsubstituted and the phenyl part is unsubstituted or has at least one substituent selected from the group consisting of methyl groups and methoxy groups.

7. The compound of claim 4, selected from the group consisting of 8-benzyl-7,8-dihydro-5-methyl-6H-pyrazolo-[1,5-a]pyrrolo[3,2-e]pyrimidine and pharmaceutically acceptable salts thereof.

8. The method of claim 3, wherein the active agent is selected from the group consisting of 8-benzyl-7,8-dihydro-5-methyl-6H-pyrazolo[1,5-a]pyrrolo[3,2-e]pyrimidine and pharmaceutically acceptable salts thereof.

* * * * *

UNITED STATES PATENT AND TRADEMARK OFFICE
CERTIFICATE OF CORRECTION

PATENT NO. : 5,086,057

DATED : February 4, 1992

INVENTOR(S) : TAKIGUCHI et al

It is certified that error appears in the above-identified patent and that said Letters Patent is hereby corrected as shown below:

Item [19],
Title page, top left-hand corner, under
"United States Patent", delete "Sasagawa"
and insert --Takiguchi et al--.

Title page, No. [57] ABSTRACT, delete the printed Abstract
and replace with
--            ABSTRACT Compounds of formula (Ib):

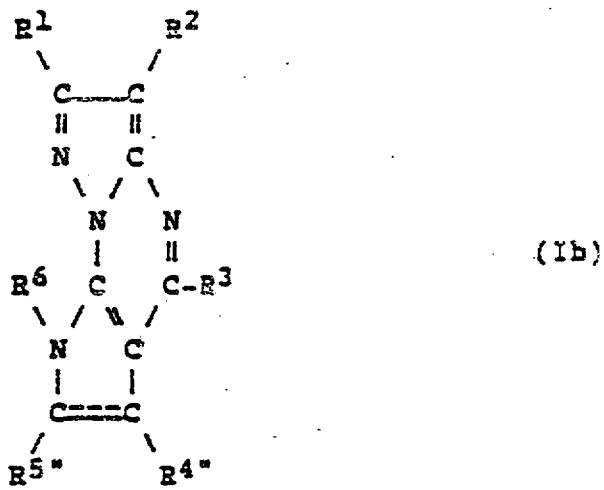

UNITED STATES PATENT AND TRADEMARK OFFICE
CERTIFICATE OF CORRECTION

PATENT NO. : 5,086,057
DATED : February 4, 1992
INVENTOR(S) : TAKIGUCHI et al

It is certified that error appears in the above-identified patent and that said Letters Patent is hereby corrected as shown below:

in which the dotted line is a double or single bond; $R^1$ is hydrogen, alkyl or aryl; $R^2$ is hydrogen or halogen; $R^3$ is alkyl or cycloalkyl; $R^4$ is hydrogen, or halogen; $R^{4'''}$ is hydrogen, or, but only when the dotted line represents a double bond, hydrogen or halogen; $R^{5'''}$ is hydrogen, or, but only when the dotted line represents a double bond, hydrogen or halogen; and $R^6$ is hydrogen, optionally substituted alkyl, alkenyl, alkynyl, cycloalkyl, aryl, or aralkyl and pharmaceutically acceptable salts thereof. The invention also provides a method of treating cachexia with these compounds and salts.--

Column 31, line 49, (claim 1), in the lower part of the formula (Ib), delete "C___C" and insert -- C≡C --.

Column 33, line 40, (claim 4), in the lower part of the formula (Ib), delete "C___C" and insert -- C≡C --.

Signed and Sealed this

Twentieth Day of September, 1994

Attest:

BRUCE LEHMAN

*Attesting Officer*    Commissioner of Patents and Trademarks